United States Patent
Connett-Porceddu et al.

(10) Patent No.: US 6,518,485 B1
(45) Date of Patent: *Feb. 11, 2003

(54) PARTICLE-MEDIATED CONIFER TRANSFORMATION

(75) Inventors: Marie Bernice Connett-Porceddu, Summerville, SC (US); Michael Ryan Becwar, Summerville, SC (US); Robert John Kodrzycki, Summerville, SC (US); Sarah Grace Schwuchow, Hollywood, SC (US)

(73) Assignee: Westvaco Corporation, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 39 days.

(21) Appl. No.: 09/318,136

(22) Filed: May 25, 1999

Related U.S. Application Data

(60) Provisional application No. 60/087,966, filed on Jun. 4, 1998.

(51) Int. Cl.[7] ............................. A01H 1/00; C12N 5/02; C12N 5/04; C12N 15/82; C12N 15/87
(52) U.S. Cl. .................. 800/293; 800/319; 435/419; 435/420; 435/431; 435/470; 435/422
(58) Field of Search ................. 435/410, 419, 435/420, 422, 440, 468, 470; 800/278, 293

(56) References Cited

U.S. PATENT DOCUMENTS

| | | | |
|---|---|---|---|
| 4,672,035 A | * | 6/1987 | Davidonis ............... 435/240 |
| 4,693,976 A | | 9/1987 | Schilperoort et al. |
| 4,886,937 A | | 12/1989 | Sederoff et al. |
| 4,945,050 A | | 7/1990 | Sandford et al. |
| 5,122,466 A | | 6/1992 | Stomp et al. |
| 5,413,930 A | | 5/1995 | Becwar et al. |
| 5,491,090 A | | 2/1996 | Handley et al. |
| 5,506,136 A | | 4/1996 | Becwar et al. |
| 5,565,355 A | | 10/1996 | Smith |
| 5,677,185 A | | 10/1997 | Handley |
| 5,681,730 A | | 10/1997 | Ellis |
| 5,731,191 A | | 3/1998 | Rutter et al. |
| 5,731,203 A | | 3/1998 | Handley |
| 5,731,204 A | | 3/1998 | Rutter et al. |
| 5,773,689 A | | 6/1998 | Thompson et al. |

FOREIGN PATENT DOCUMENTS

| | | |
|---|---|---|
| NZ | 336149 | 2/2001 |
| WO | 9701641 | 1/1997 |
| ZA | 99/3748 | 2/2000 |

OTHER PUBLICATIONS

Becwar M. R., and G. S. Pullman. 1995. Somatic embryogenesis in loblolly pine (*Pinus taeda* L.). In: Somatic embryogenesis in woody plants, vol. 3. Edited by S. Jain, P. Gupta, and R. Newton. Kluwer Academic Publishers, The Netherlands. pp. 287–301.

(List continued on next page.)

*Primary Examiner*—Elizabeth F. McElwain
*Assistant Examiner*—Cynthia Collins
(74) *Attorney, Agent, or Firm*—Daniel B. Reece IV; Terry B. McDaniel; Richard L. Schmalz

(57) ABSTRACT

This invention relates to a method for genetically engineering coniferous plants. In particular, this invention relates to a particle-mediated gene transfer method for producing and developing transgenic somatic embryos for plants of the genus Pinus and Pinus interspecies hybrids. This method is well suited for producing transgenic clonal planting stock useful for reforestation.

18 Claims, 1 Drawing Sheet

OTHER PUBLICATIONS

Campbell, M. A., C. S. Kinlaw, and D. B. Neale. 1992. Expression of luciferase and β–glucuronidase in *Pinus radiata* suspension cells using electroporation and particle bombardment. Canadian Journal of Forest Research 22(12)2014–2018.

Charest, P. J., N. Calero, D. Lachance, R. S. S. Datla, L. C. Duchesne, and E. W. T. Tsang. 1993. Microprojectile–DNA delivery in conifer species: factors affecting assessment of transient gene expression using the β–glucuronidase reporter gene. Plant Cell Reports 12: 189–193.

Clapham, D., G. Manders, H. S. Yibrah and S. von Arnold. 1995. Enhancement of short– and medium–term expression of transgenes in embryogenic suspensions of *Picea abies* (L.) Karst. Journal of Experimental Botany 46: 655–662.

Hackman, I. and L. C. Fowke. 1987. Somatic embryogenesis in *Picea glauca* (white spruce) and *Picea mariana* (black spruce). Canadian Journal of Botany 65:656–659.

Hakman, I. and S. von Arnold, 1988. Somatic embryogenesis and plant regeneration from suspension cultures of *Picea glauca* (White spruce). Physiologia Plantarum 72:579–587.

von Arnold, S. and T. Eriksson. 1981. In vitro studies of adventitious shoot formation in *Pinus contorta*. Canadian Journal of Botany 59:870–874.

von Arnold, S. and I. Hakman. 1988. Regulation of somatic embryo development in *Picea abies* by abscisic acid (ABA). Journal of Plant Physiology 132:164–169.

Walter, C., D. R. Smith, M. B. Connett, L. Grace and D. W. R. White. 1994. A Biolistic approach for the transfer and expression of a gusA reporter gene in embryogenic cultures of *Pinus radiata*. Plant Cell Reports 14: 69–74.

Webb, D. T., F. Webster, B. S. Flinn, D. R. Roberts, and D. D. Ellis. 1989. Factors influencing the induction of embryogenic and caulogenic callus from embryos of *Picea glauca* and *P. engelmanii*. Canadian Journal of Forest Research 19:1303–1308.

Loopstra, C. A., R. R. Sederoff. 1990. Gene Expression in Xylem of Loblolly Pine. Meeting of the International Union of Forestry Research Organizations Molecular Genetics Working Party S2.04.06. Institute of Forest Genetics.

Robertson, D., A. K. Weissinger, R. Ackley, S. Glover and R. R. Sederoff. 1992. Genetic transformation of Norway spruce (*Picea abies*(L.) Karst) using somatic embryo explants by microprojectile bombardment. *Plant Molecular Biology* 19:925–935.

Tsang E. W. T., P. J. Charest, and R. R. Sederoff. 1995. Genetic Transformation in Conifers. In: Recent Progress in Forest Biotechnology in Canada. (P. J. Charest and L. C. Duchesne, eds.) Petawawa National Forestry Institute. Information Report PI–X–120. pp. 16–28.

* cited by examiner

PARTICLE-MEDIATED CONIFER TRANSFORMATION

This application claims the benefit of U.S. Provisional Application Ser. No. 60/087,966, filed Jun. 4, 1998.

FIELD OF INVENTION

This invention relates to a method for genetically engineering coniferous plants. In particular, this invention relates to a particle-mediated gene transfer method for producing and developing transgenic embryos for plants of the genus Pinus and Pinus interspecies hybrids. This method is well suited for producing transgenic clonal planting stock useful for reforestation.

BACKGROUND OF THE INVENTION

The identification of gene function coupled with the ability to precisely manipulate DNA has enabled the construction of synthetic genes which, when properly transferred and incorporated into a host cell, can modify the cell's genetic makeup. This capacity to manipulate genes using recombinant DNA technology combined with in vitro methods for plant propagation now permits genetic engineering of crop species. Indeed, genetic engineering processes have been used to successfully transfer foreign genes into certain plant species, thereby resulting in the recipient species acquiring a useful genetic trait (such as resistance to herbicides or insects).

The transfer of foreign genetic material into the chromosomes of a recipient plant is typically carried out through the use of either an Agrobacterium-mediated or a particle-mediated transformation process. Agrobacterium gene transfer employs the natural ability of the soil-borne bacterium *Agrobacterium tumefaciens* to transfer a portion of DNA (known as T-DNA) from an extrachromosomal plasmid (known as the Ti-plasmid) to a receptive plant host cell under specific conditions. Using suitable techniques of recombinant DNA manipulation, the T-DNA may be replaced with a desired piece of DNA. This method has not proven suitable for all plant cell types.

In particle-mediated gene transfer, the DNA of interest is precipitated onto the surface of carrier particles which are subsequently accelerated toward a piece of target tissue. The carrier particles penetrate the cell wall of the plant cell, wherein the DNA can be expressed, and may integrate with the chromosomal DNA. Transient expression of the transforming DNA has been reported in conifers (Charest et al., 1993; Walter et al., 1994). Stable expression only results if the transforming DNA integrates with the chromosomal DNA.

In addition to Agrobacterium-mediated and particle-mediated gene transfer, other methods of gene transfer have been used to introduce foreign genes into conifers, such as electroporation (Campbell et al., 1992). However, only transient expression has been reported using any of these other methods, and no transgenic plants have been reported to have been generated using such methods.

This illustrates that the mere act of introducing DNA into the host cell chromosome is, by itself, not sufficient for the production of transgenic plants. A tissue culture system that enables the multiplication and subsequent development of the transformed cells is also an important component of a successful genetic transformation protocol.

A method known as somatic embryogenesis is sometimes employed in the clonal propagation of certain conifers. Propagation by somatic embryogenesis refers to methods whereby embryos are produced in vitro from small pieces of plant tissue or individual cells. The embryos are referred to as somatic because they are derived secondarily, from somatic (vegetative) tissue, rather than directly from the sexual process. Vegetative propagation via somatic embryogenesis has the capability to capture the genetic gain of highly desirable genotypes. Furthermore, these methods may be readily amenable to automation and mechanization to produce large numbers of plants of individual clones (e.g. for reforestation purposes).

It was not until 1985 that somatic embryogenesis was demonstrated in conifers and the first viable plantlets were regenerated from conifer somatic embryos. Since 1985, conifer tissue culture workers throughout the world have pursued the development of somatic embryogenesis systems capable of regenerating plants. The goal of much of this work is to develop conifer somatic embryogenesis as an efficient propagation system for producing clonal planting stock en masse.

The two most economically important conifer genera are Picea (spruce) and Pinus (pine). Those working in conifer somatic embryogenesis have found that there is a striking difference between Picea conifers and Pinus conifers as to the ease with which somatic embryogenesis can be initiated and plants regenerated. In fact, when one measures the respective levels of achievement in the art of conifer somatic embryogenesis among species of these two important genera, it is clear that significantly more success has been obtained with Picea than with Pinus. Indeed, the recalcitrance of embryogenic cultures of Pinus species is well documented. This is especially true for pines commonly found in the southeastern United States (known in the industry as Southern yellow pines).

Nevertheless, researchers working with Pinus species plants have recently achieved some important advances. For example, U.S. Pat. Nos. 5,413,930, 5,491,090, 5,506,136, 5,677,185, 5,731,191, 5,731,203, and 5,731,204 (which are hereby incorporated by reference) disclose multi-step methods that are able to complete the entire somatic embryogenesis regenerative process, from explant collection to planting of somatic embryo derived plants, for historically recalcitrant Southern yellow pines (i.e., *Pinus taeda, Pinus serotina, Pinus palustris*, and *Pinus elliottii*), *Pinus rigida*, and hybrids thereof Scientists have found the dichotomy exhibited by Picea conifers and Pinus conifers in the area of somatic embryogenesis also exists in the field of genetic engineering. While researchers have been able to stably genetically transform Picea conifers, Pinus conifers—and particularly Southern yellow pines—have proven to be extremely resistive to such modifications. Indeed, the relative ease of genetic transformation of Picea conifers in comparison to Pinus conifers is evident when examining the reports in the literature describing the success of Picea transformation in somatic embryogenic systems and the paucity of such reports for Southern yellow pines.

Although researchers have been able to routinely attain stable particle-mediated genetic transformations in Picea conifers, historically almost all of such transformations reported in Pinus conifers, particularly Southern yellow pines, have, upon examination, been found to be transient transformations or transformation of tissue which was not subsequently regenerable into whole plants. While transient, or non-integrative, transformation can be achieved easily in many tissues and stages of Pinus embryo development, the ability to achieve stable transformation in a tissue capable of producing whole plants is the key to a successful gene transfer system.

It has been found that a successful stable genetic transformation protocol is heavily dependant on the employment of an efficient tissue culture system. Moreover, efficient tissue culture methods must be coordinated with gene transfer at a receptive stage of embryo development in order to achieve stable genetic transformations. The stage of development at which transformation has been carried out in order to attain the regeneration of transgenic plants in Picea conifers (i.e. in embryogenic tissues initiated from cotyledonary embryos) does not give rise to embryogenic tissues capable of regenerating whole plants in conifers of the genus Pinus. Furthermore, in Picea conifers embryogenic tissues initiated from earlier stage embryos, such as pre-stage 3 somatic embryos, have not given rise to transformed plants. Indeed, the methods taught by Ellis in U.S. Pat. No. 5,681,730 for obtaining and genetically transforming somatic embryos in Picea conifers have not been found effective when applied to Pinus conifers. However, in the genus Pinus we have found that transformation steps can be successfully combined with a tissue culture system to derive embryogenic cultures from pre-stage 3 somatic embryos, pre-stage 3 zygotic embryos or somatic embryogenic tissue containing pre-stage 3 somatic embryos which are capable of regenerating whole transgenic plants.

It has long been known to those skilled in the art of transformation that a brief osmotic treatment at the time of transformation will increase transient expression of the transgene. In conifers, a treatment with elevated levels of inositol has been shown to be of benefit in transformation of white spruce, *Picea glauca* (Clapham et al. 1995). However, in *Pinus taeda* and *P. taeda×P. rigida* hybrids, the same treatment with elevated levels of inositol (i.e., levels greater than about 0.2 M) is detrimental to both growth and embryo development. In *Pinus radiata*, a pretreatment with sorbitol increased transient expression of a transgene (Walter et al. 1994), but such a pre-treatment has not been taught for obtaining stable expression and regeneration of transformed pine plants (Walter et al. 1997), perhaps because such treatments can also be detrimental to the regeneration of pine plants. To address these problems in the genus Pinus, we have developed a variety of preparation media for use before transformation and selection in pines. The use of the preparation media facilitated the recovery and development of stable genetically transformed embryos.

Therefore, an object of the present invention is to provide a method of genetically engineering plants of the genus Pinus and Pinus interspecies hybrids.

Another object of the present invention is to provide a method for stably transforming embryogenic tissues of the genus Pinus and Pinus interspecies hybrids.

A further object of the invention is to produce stably transformed embryos of the genus Pinus and Pinus interspecies hybrids capable of further development into transgenic plants.

Yet another object of the present invention is to produce genetically engineered plants of the genus Pinus and Pinus interspecies hybrids.

SUMMARY OF THE INVENTION

The above objectives are achieved via the use of a particle-mediated genetic transformation method which employs embryogenic tissues from plants of the genus Pinus and Pinus interspecies hybrids. This method involves the use of particle-mediated gene transfer with embryogenic tissues which are in a particular stage of development, namely pre-stage 3 somatic embryos, pre-stage 3 zygotic embryos, or somatic embryogenic tissue containing pre-stage 3 somatic embryos. It is preferred to accomplish this by employing a multi-step method which: a) prepares pre-stage 3 (i.e., pre-cotyledonary) somatic embryos, pre-stage 3 zygotic embryos, and/or somatic embryogenic tissue containing pre-stage 3 somatic embryos as the receptive target tissue for gene transfer via culturing the target tissue on preparation media, b) employs particle-mediated gene transfer to insert DNA into the target tissue, and c) exposes the bombarded tissue to selection media in order to identify and develop transformed embryogenic lines. Where desired, additional steps can be utilized to both cryopreserve such lines and to develop the transformed embryogenic lines into plants.

This method results in recovery of transgenic events through all stages of the transformation process leading to the production of transgenic pine trees (even historically recalcitrant Southern pines). This method also allows the transfer of genetic material to embryogenic cultures that may be used to establish clonal plantations of pine trees that are improved economically through expression of the transferred genetic material. This method further permits the development of transgenic embryos from embryogenic tissue which has been cryopreserved.

The invention also encompasses the genetically transformed embryos produced via the method and the transgenic plants derived therefrom.

DESCRIPTION OF THE DRAWINGS

The Figures represent genetic constructions (plasmid DNA) employed in the Examples for Biolistic transformation of pine cell cultures.

DESCRIPTION OF THE PREFERRED EMBODIMENT

Figure 1A:
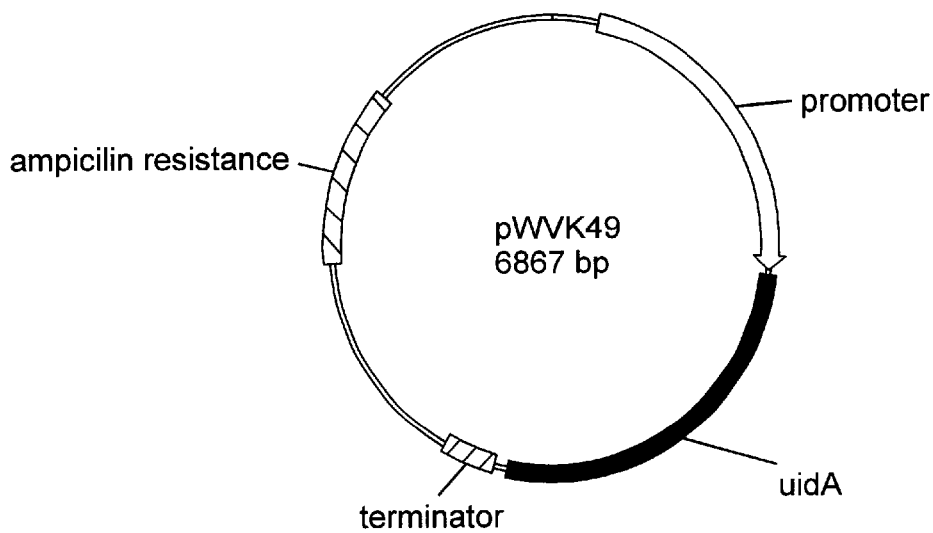
FIG. 1A represents the plasmid pWVK49 which contains a synthetic gene consisting of a plant promoter sequence, a coding sequence for the visual marker gene uidA from *Escherichia coli*, and a gene terminator sequence.

The importance of the developmental stage of the explant tissue used to initiate embryogenic cultures in conifers varies considerably among different species. In spruces, for example, cultures can be initiated from a wide range of embryo developmental stages (i.e., immature, mature and germinating embryos). However, pines have proven much more restricted than spruces in terms of the responsive embryo development stage for somatic embryogenic culture initiation. To be successful in pines, one must use only very immature embryos (or seeds containing such immature embryos). The size of the developing embryo, usually measured as length, has frequently been used to determine the appropriate developmental stage for culture initiation in many plant species. This has been the case with loblolly pine where it was found that the embryogenic culture initiation occurred most frequently when the dominant zygotic embryo was less than about 0.5 mm in length.

Because it is difficult to measure the size of very immature differentiated embryos, embryo staging systems have also been used to make the determination of the appropriate developmental stage easier. These staging systems are based on several factors, including various morphological characteristics of the embryo. An embryo staging system proposed by Hakman and von Arnold (1988), which is commonly utilized in the industry, has the following three distinct stages. Stage 1 embryos are small differentiated embryos consisting of an embryonic region of small, densely cytoplasmic region subtended by a suspensor comprised of long, highly vacuolated cells. Stage 2 embryos are further differentiated embryos with a prominent embryonic region that becomes more opaque and assumes a smooth and glossy surface. Stage 3 embryos are further differentiated embryos which show visible cotyledonary primordia. Thus, stage 1 and 2 embryos are at a pre-cotyledonary stage of development, while stage 3 embryos are cotyledonary. As used herein, the term "pre-stage 3 embryo" means a differentiated pre-cotyledonary embryo (i.e., a stage 1 or stage 2 embryo). Although the above three-stage system was first used with somatic embryos of spruce, it is generally applicable to both somatic and zygotic embryos of all conifer species.

The present invention is a method for genetically engineering conifers selected from the group consisting of the genus Pinus and Pinus interspecies hybrids, which comprises:

(a) placing conifer target tissue selected from the group consisting of embryogenic tissue containing pre-stage 3 somatic embryos, pre-stage 3 somatic embryos, pre-stage 3 zygotic embryos, and combinations thereof, on a target surface;

(b) bombarding the target tissue by physically accelerating at the target tissue carrier particles which are much smaller than the cells of the target tissue, the carrier particles carrying copies of a genetic construction including at least one gene of interest;

(c) inducing the bombarded target tissue to form proliferative tissue which is capable of forming somatic embryos;

(d) during the step of inducing, culturing the bombarded target tissue on selection medium so as to select for embryogenic tissue which is transformed by the gene of interest;

(e) inducing transformed somatic embryos to develop from the selected embryogenic tissue; and (f) germinating and converting the transformed somatic embryos thus produced into clonal transgenic conifer plants.

It has been found that the employment of preparation media greatly facilitates the recovery and development of stable genetically transformed embryos. It is, therefore, preferred that the conifer target tissue be cultured under suitable environmental conditions on preparation media prior to be placed on the target surface for bombardment by the carrier particles (normally for a period up to about 60 days). Likewise, it is preferred that the bombarded target tissue be cultured on preparation media following insertion of the carrier particles for a period of time sufficient to allow tissue recovery. It is more preferred to both: a) prepare the conifer target tissue for carrier particle bombardment by culturing the target tissue on preparation media prior to bombarding the tissue, and b) culture the bombarded target tissue on preparation media following bombardment in order to facilitate tissue recovery.

A further preferred method for genetically engineering conifers selected from the group consisting of the genus Pinus and Pinus interspecies hybrids comprises:

(a) placing a suitable conifer explant on culture initiation medium containing a sufficient amount of inorganic and organic nutrients, about 0.1 to about 5.0 mg/l of auxin, about 0.1 to about 1.0 mg/l of cytokinin, up to about 100.0 mg/l of abscisic acid, about 5.0 to about 100.0 g/l of sugar, and a gelling agent selected from the group consisting of about 2.5 to about 9.0 g/l of agar, about 0.5 to about 4.0 g/l of gellan gum, about 3.0 to about 10.0 g/l of agarose, about 1.5 to about 5.0 g/l of AGARGEL, and combinations thereof, for a sufficient amount of time under suitable environmental conditions to grow an embryogenic tissue culture containing pre-stage 3 somatic embryos;

(b) placing target tissue from the embryogenic tissue culture on a target surface, wherein the placed target tissue is selected from the group consisting of embryogenic tissue containing pre-stage 3 somatic embryos, pre-stage 3 somatic embryos, and combinations thereof;

(c) bombarding the target tissue by physically accelerating at the target tissue carrier particles which are much smaller than the cells of the target tissue, the carrier particles carrying copies of a genetic construction including at least one gene of interest;

(d) transferring the bombarded target tissue to selection medium so as to select for embryogenic tissue which is transformed by the gene of interest;

(e) transferring the transformed embryogenic tissue to embryo development medium containing a sufficient amount of inorganic and organic nutrients, about 5.0 mg/l to about 300.0 mg/l of abscisic acid with the continued maintenance of the abscisic acid concentration, up to about 10.0 g/l of activated carbon, about 20.0 to about 70.0 g/l of sugar, and a gelling agent selected from the group consisting of about 6.0 to about 12.0 g/l of agar, about 1.75 to about 4.0 g/l of gellan gum, about 6.0 to about 8.0 g/l of agarose, about 3.5 to about 6.0 g/l of AGARGEL, and combinations thereof, for a sufficient time under suitable environmental conditions to develop transgenic stage 3 somatic embryos;

(f) separating the transgenic stage 3 somatic embryos from the development medium and partially drying the embryos by exposing the embryos to an atmosphere having a high relative humidity for a period of about 2 to about 5 weeks;

(g) transferring the partially dried transgenic embryos to germination medium containing a sufficient amount of organic and inorganic nutrients, up to about 10.0 g/l of activated carbon, about 20.0 to about 40.0 g/l of sugar, and a gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, for a sufficient time under suitable environmental conditions to germinate the partially dried transgenic embryos;

(h) converting the germinated transgenic embryos into acclimatized transgenic conifer plants; and (i) field planting the acclimatized transgenic conifer plants.

A further preferred method for genetically engineering conifers selected from the group consisting of the genus Pinus and Pinus interspecies hybrids comprises:

(a) placing conifer target tissue selected from the group consisting of pre-stage 3 zygotic embryos, tissues extruded from immature megagameophytes which contain pre-stage 3 zygotic embryos, and combinations thereof, on a target surface;

(b) bombarding the target tissue by physically accelerating at the target tissue carrier particles which are much smaller than the cells of the target tissue, the carrier particles carrying copies of a genetic construction including at least one gene of interest;

(c) transferring the bombarded target tissue to selection medium so as to select for embryogenic tissue which is transformed by the gene of interest;

(d) transferring the transformed embryogenic tissue to embryo development medium containing a sufficient amount of inorganic and organic nutrients, about 5.0 mg/l to about 300.0 mg/l of abscisic acid with the continued maintenance of the abscisic acid concentration, up to about 10.0 g/l of activated carbon, about 20.0 to about 70.0 g/l of sugar, and a gelling agent selected from the group consisting of about 6.0 to about 12.0 g/l of agar, about 1.75 to about 4.0 g/l of gellan gum, about 6.0 to about 8.0 g/l of agarose, about 3.5 to about 6.0 g/l of AGARGEL, and combinations thereof, for a sufficient time under suitable environmental conditions to develop transgenic stage 3 somatic embryos;

(e) separating the transgenic stage 3 somatic embryos from the development medium and partially drying the embryos by exposing the embryos to an atmosphere having a high relative humidity for a period of about 2 to about 5 weeks;

(f) transferring the partially dried transgenic embryos to germination medium containing a sufficient amount of organic and inorganic nutrients, up to about 10.0 g/l of activated carbon, about 20.0 to about 40.0 g/l of sugar, and a gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, for a sufficient time under suitable environmental conditions to germinate the partially dried transgenic embryos;

(g) converting the germinated transgenic embryos into acclimatized transgenic conifer plants; and (h) field planting the acclimatized transgenic conifer plants.

These methods are generally applicable to tissue obtained from the Pinus species including, but not limited to, the following: Pinus taeda (loblolly pine), P. elliottii (slash pine), P. palustris (longleaf pine), P. serotina (pond pine), P. echinata (shortleaf pine), P. clausa (sand pine), P. glabra (spruce pine), P. rigida (pitch pine), P. echinata (shortleaf pine), P. nigra (Austrian pine), P. resinosa (red pine), P. sylvestris (Scotch pine), P. banksiana (jack pine), P. virginiana (Virginia pine), P. radiata (Monterey pine), P. contorta (shore pine), P. contorta latifolia (lodgepole pine), P. ponderosa (ponderosa pine), P. leiophylla (Chihuahua pine), P. jeffreyi (Jeffrey pine), and P. engelmannii (Apache pine), P. strobus (eastern white pine), P. monticola (western white pine), P. lambertiana (sugar pine), P. massoniana (Masson pine), P. merkusii, P. albicaulis (whitebark pine), P. flexilis (limber pine), P. strobiformis (southwestern white pine), P. caribaea (Caribbean pine), P. patula (Mexican weeping pine), P. tecunumanii (Tecun Uman pine), P. maximinoi, P. oocarpa (Ocote Pine) and P. chiapensis (Mexican White pine). In addition, the current invention is specifically applicable to interspecies hybrids of the above mentioned pines including Pinus rigida×P. taeda, P. serotina×P. taeda, and reciprocal crosses.

It is preferred to utilize the present methods with Southern yellow pines, Pinus rigida, Pinus radiata, and hybrids thereof. Those skilled in the art recognize that several species of pine indigenous to the Southeastern United States are closely related and hybridize naturally. Taxonomically this group of pines is referred to as "Southern yellow pines" and includes Pinus taeda, P. serotina, P. palustris, and P. elliottii.

Plant tissues which are suitable for use in the present methods as target tissues for carrier particle bombardment consist of embryogenic tissues containing pre-stage 3 somatic embryos, pre-stage 3 somatic embryos, pre-stage 3 zygotic embryos, and combinations thereof. Suitable somatic embryogenic tissues contain pre-stage 3 somatic embryos having polarity, with a prominent embryonic region subtended by elongated suspensor cells, or pre-stage 3 somatic embryos obtained from these cultures. As used herein, the term "pre-stage 3 somatic embryo" means a differentiated somatic embryo which is at a pre-cotyledonary stage of development. That is, the embryo is continuing to differentiate, but cotyledonal primordia are not yet outwardly visible. Likewise, the term "pre-stage 3 zygotic embryo" means a differentiated zygotic embryo which is at such a pre-cotyledonary stage of development.

Where desired, zygotic embryos which are suitable for use in the present invention can be produced by isolating the pre-stage 3 zygotic embryos from immature seeds. Likewise, newly extruded pre-stage 3 zygotic embryos from recently cultured immature seeds may be employed as target tissue for genetic transformation. Alternatively, immature seeds which contain immature zygotic embryos at the desired pre-stage 3 development can be used as targets for genetic transformation. Where the conifer target tissue consists of immature megagameophytes which contain pre-stage 3 zygotic embryos, it is preferred to culture the bombarded target tissue in order to encourage the extrusion of the bombarded pre-stage 3 zygotic embryos, which are subsequently transferred to selection medium (thereby enabling the selection of embryogenic tissue cells which has been transformed by the gene of interest). Media which are suitable for culturing the bombarded target tissue include the culture initiation media taught herein, and the like.

Appropriate somatic embryogenic tissues can be produced by placing a suitable explant on nutrient-containing culture media for a sufficient amount of time under suitable environmental conditions to develop a culture containing somatic embryogenic tissue and/or pre-stage 3 somatic embryos.

Explants which are suitable for use in the present methods include immature zygotic embryos, megagametophytes containing immature zygotic embryos, and the like.

It is preferred that the somatic embryogenic tissues be produced by first initiating tissue growth via placing a suitable explant on culture initiation medium containing a sufficient amount of inorganic and organic nutrients, about 0.1 to about 5.0 mg/l of auxin, about 0.1 to about 1.0 mg/l of cytokinin, up to about 100.0 mg/l of abscisic acid, about 5.0 to about 100.0 g/l of sugar, and a level of gelling agent selected from the group consisting of about 2.5 to about 9.0 g/l of agar, about 0.5 to about 4.0 g/l of gellan gum, about 3.0 to about 10.0 g/l of agarose, about 1.5 to about 5.0 g/l of AGARGEL, and combinations thereof, for a sufficient amount of time (normally about 2 to 14 weeks) under suitable environmental conditions to grow a somatic embryogenic culture containing somatic embryogenic tissue and/or pre-stage 3 somatic embryos.

Sugars which are suitable for use in the present methods include, but are not limited to, the following: glucose, maltose, sucrose, and combinations thereof.

Where desired, one may culture the embryogenic tissue culture and/or pre-stage 3 somatic embryos by transferring the somatic embryogenic culture from the culture initiation medium to culture maintenance medium containing a sufficient amount of inorganic and organic nutrients, about 0.1 to about 5.0 mg/l of auxin, about 0.1 to about 1.0 mg/l of cytokinin, up to about 100.0 mg/l of abscisic acid, up to about 10.0 g/l of activated carbon, and about 10.0 to about 40.0 g/l of sugar, for a sufficient time under suitable environmental conditions to grow the embryogenic tissue culture.

Where desired, one may culture the bombarded target tissue on culture maintenance media containing a sufficient amount of inorganic and organic nutrients, about 0.1 to about 5.0 mg/l of auxin, about 0.1 to about 1.0 mg/l of cytokinin, up to about 100.0 mg/l of abscisic acid, up to about 10.0 g/l of activated carbon, and about 10.0 to about 40.0 g/l of sugar for a sufficient time under suitable environmental conditions to grow the bombarded target tissue.

Where desired, one may culture the transformed embryogenic tissue on culture maintenance media containing a sufficient amount of inorganic and organic nutrients, about 0.1 to about 5.0 mg/l of auxin, about 0.1 to about 1.0 mg/l of cytokinin, up to about 100.0 mg/l of abscisic acid, up to about 10.0 g/l of activated carbon, and about 10.0 to about 40.0 g/l of sugar for a sufficient time under suitable environmental conditions to grow the transformed embryogenic tissue.

Where desired, the culture maintenance media may further contain a gelling agent selected from the group consisting of about 6.0 to about 9.0 g/l of agar, about 1.75 to about 4.0 g/l of gellan gum, about 6.0 to about 8.0 g/l of agarose, about 3.5 to about 5.0 g/l of AGARGEL, and combinations thereof.

Where desired, the embryogenic tissue culture from the culture initiation medium may be cultured on embryo development medium containing a sufficient amount of inorganic and organic nutrients, about 5.0 mg/l to about 300.0 mg/l of abscisic acid with the continued maintenance of the abscisic acid concentration, up to about 10.0 g/l of activated carbon, about 20.0 to about 70.0 g/l of sugar, and a gelling agent selected from the group consisting of about 6.0 to about 12.0 g/l of agar, about 1.75 to about 4.0 g/l of gellan gum, about 6.0 to about 8.0 g/l of agarose, about 3.5 to about 6.0 g/l of AGARGEL, and combinations thereof, for a sufficient time under suitable environmental conditions to prepare the target tissue for carrier particle bombardment.

It is preferred to culture the conifer target tissue under suitable environmental conditions on preparation media prior to the bombardment of the tissue by the carrier particles in order to prepare the tissue for particle insertion. It is also preferred to culture the bombarded target tissue under suitable environmental conditions on preparation media prior to transferring the bombarded tissue to selection media in order to facilitate tissue recovery from the bombardment. It is more preferred to both culture the target tissue on preparation media prior to bombarding the tissue, and to culture the bombarded tissue on preparation media following the carrier particle bombardment.

Preparation media suitable for use in the present methods contain sufficient inorganic and organic nutrients, up to about 5.0 mg/l of auxin, up to about 1.0 mg/l of cytokinin, up to about 150.0 mg/l of abscisic acid, about 10.0 to about 120.0 g/l of sugar, and up to about 0.5M of organic alcohol. When such liquid preparation media are employed, it is necessary to disperse the target tissue on a target surface (i.e., a solid support or a gelled medium) to allow particles to be accelerated toward it. Normally this dispersion occurs about 1 to 72 hours prior to particle bombardment.

Where desired, the preparation medium may further contain a gelling agent selected from the group consisting of about 6.0 to about 9.0 g/l of agar, about 1.75 to about 5.0 g/l of gellan gum, about 6.0 to about 8.0 g/l of agarose, about 3.5 to about 5.0 g/l of AGARGEL, and combinations thereof.

Organic alcohols which are suitable for use in the present method include, but are not limited to, the following: glycerol, mannitol, sorbitol, polyethylene glycol, and combinations thereof.

Gene transfer is carried out via particle-mediated transfer in which a DNA genetic construction containing at least one gene of interest is precipitated onto the surface of a carrier particle (microparticle) and accelerated toward the conifer target tissue. If desired, isolated pre-stage 3 somatic embryos and/or isolated pre-stage 3 zygotic embryos can be utilized as target tissue. The common procedures for particle-mediated transfers are well-known to those skilled in the art of genetic engineering, as evidenced by U.S. Pat. No. 4,945,050 to Sandford et al. (which is hereby incorporated by reference). It is preferred to utilize a helium-driven apparatus for the insertions. It is also preferred to employ microparticles between 0.2 and 2.0 microns in diameter as carrier particles.

Where the DNA genetic construction that is being transferred contains a selection gene, the target tissue may be submitted to selective pressure to inhibit the growth of any non-transgenic (i.e., non-transformed) cells. As used herein, a selection gene is defined as a gene whose activity allows cells to grow well in a selection culture medium only if the cells have incorporated the gene, while cells which have not incorporated the gene grow more slowly, do not grow, or are killed. Culture selection media which are suitable for use in the present method incorporate a toxin to which the selection gene confers resistance, or are composed such that a component necessary for growth of cells is absent and must be provided by the cells that have incorporated the selection gene, or are composed such that a component necessary for growth is present in a form which can only be taken up or metabolized by cells which have incorporated the selection gene.

A selection medium suitable for use in the present method contains a sufficient amount of organic and inorganic nutrients, a selection agent at a concentration which is toxic to non-transformed cells but for which the gene of interest confers resistance to transformed cells, up to about 5.0 mg/l of auxin, up to about 1.0 mg/l of cytokinin, up to about 30.0 mg/l of abscisic acid, and up to about 60.0 g/l of sugar.

Another selection medium suitable for use in the present method contains a sufficient amount of organic and inorganic nutrients, up to about 5.0 mg/l of auxin, up to about 1.0 mg/l of cytokinin, up to about 30.0 mg/l of abscisic acid, up to about 60.0 g/l of sugar, and wherein the selection medium lacks a component necessary for the growth of non-transformed cells but for which the gene of interest confers to transformed cells the ability to produce the lacking component.

Another selection medium suitable for use in the present method contains a sufficient amount of organic and inorganic nutrients, up to about 5.0 mg/l of auxin, up to about 1.0 mg/l of cytokinin, up to about 30.0 mg/l of abscisic acid, up to about 60.0 g/l of sugar, and wherein the selection medium contains a component necessary for the growth of cells in a form which cannot be utilized by non-transformed cells but for which the gene of interest confers to transformed cells the ability to utilize the necessary component.

Another selection medium suitable for use in the present method contains a sufficient amount of organic and inorganic nutrients, up to about 5.0 mg/l of auxin, up to about 1.0 mg/l of cytokinin, up to about 30.0 mg/l of abscisic acid, up to about 60.0 g/l of sugar, and wherein the selection medium allows preferential growth of transformed cells containing the gene of interest.

Where desired, the selection medium may further contain a gelling agent selected from the group consisting of about 6.0 to about 9.0 g/l of agar, about 1.75 to about 4.0 g/l of gellan gum, about 6.0 to about 8.0 g/l of agarose, about 3.5 to about 5.0 g/l of AGARGEL, and combinations thereof.

It is preferred to transfer the transformed embryogenic tissue to embryo development medium containing a sufficient amount of inorganic and organic nutrients, about 5.0 mg/l to about 300.0 mg/l of abscisic acid with the continued maintenance of the abscisic acid concentration, up to about 10.0 g/l of activated carbon, about 20.0 to about 70.0 g/l of sugar, and a gelling agent selected from the group consisting of about 6.0 to about 12.0 g/l of agar, about 1.75 to about 4.0 g/l of gellan gum, about 6.0 to about 8.0 g/l of agarose, about 3.5 to about 6.0 g/l of AGARGEL, and combinations thereof, for a sufficient time under suitable environmental conditions to develop transgenic stage 3 somatic embryos;

It is further preferred to add up to about 100.0 g/l of polyethylene glycol to the embryo development medium; and to subsequently transfer the transgenic stage 3 embryos from the embryo development medium to a second development medium containing a sufficient amount of inorganic and organic nutrients, about 5.0 mg/l to about 300.0 mg/l of abscisic acid with the continued maintenance of the abscisic acid concentration, up to about 10.0 g/l of activated carbon, up to about 100.0 g/l of polyethylene glycol, and about 20.0 to about 70.0 g/l of sugar, for a sufficient time under suitable environmental conditions to further develop the transgenic stage 3 somatic embryos prior to partially drying the embryos.

It is also preferred to add of up to about 100.0 g/l of polyethylene glycol to the embryo development medium; and to subsequently transfer the transgenic stage 3 embryos from the embryo development medium to a second development medium containing a sufficient amount of inorganic and organic nutrients, up to about 100.0 mg/l of abscisic acid with the continued maintenance of the abscisic acid concentration, up to about 10.0 g/l of activated carbon, up to about 100.0 g/l of polyethylene glycol, and about 20.0 to about 70.0 g/l of sugar, for a period of about 2 to about 12 weeks at a temperature in the range of about 0° C. to about 10° C. under suitable environmental conditions to maintain the viability of the transgenic stage 3 somatic embryos prior to partially drying the embryos.

The transgenic stage 3 somatic embryos are subsequently separated from the development medium and are partially dried. It is preferred that the transgenic stage 3 embryos be partially dried or dehydrated via exposure to an atmosphere having a high relative humidity for a period of about 2 to 5 weeks. The amount of moisture to be removed an embryo depends upon several factors, including the genotype of the embryo, the culture medium used, and the storage products contained in the embryo. It is well within the ability of a skilled artisan to determine the optimum moisture loss necessary to prepare each embryo for germination.

Where desired, the partially dried transgenic somatic embryos may be transferred to germination medium. It is preferred that the germination medium contain a sufficient amount of organic and inorganic nutrients, up to about 10.0 g/l of activated carbon, about 20.0 to about 40.0 g/l of sugar, and a gelling agent selected from the group consisting of about 6.0 to about 9.0 g/l of agar, about 1.75 to about 4.00 g/l of gellan gum, about 6.0 to about 8.0 g/l of agarose, about 3.5 to about 5.0 g/l of AGARGEL, and combinations thereof, for a sufficient time under suitable environmental conditions to germinate the partially dried transgenic embryos. The germinated transgenic embryos are subsequently converted into acclimatized transgenic conifer plants and planted in soil or similar media for glasshouse or field growth.

Where desired, the target tissues, bombarded target tissues, and selected embryogenic tissues may be cryopreserved (normally via the use of liquid nitrogen) in order to maintain a bank of cultures and to insure against loss of culture genotypes due to contamination, loss of vigor associated with culture aging, or other deleterious changes that may occur during long-term culture maintenance A number of terms are known to have differing meanings when used in the literature. The following definitions are believed to be the ones most generally used in the field of botany and are consistent with the usage of the terms in the present specification.

"Conversion" refers to the acclimatization process that in vitro derived germinating somatic embryos undergo in order to survive ex vitro (nonaxenic) conditions, and subsequent continued growth under ex vitro conditions.

"Cryopreservation" is the storage of living cells at ultra-low (cryogenic) temperatures, usually in liquid nitrogen (−196° C.) or in its vapor phase (about −150° C.).

"Embryo development" is the step in the somatic embryogenesis process where the culture and/or environmental conditions are changed causing the embryogenic culture to switch from a proliferative phase of growth to a phase where somatic embryos develop to a stage where they are ready to harvest. In conifers the harvestable stage is typically stage 3 embryos having cotyledons.

"(Embryo) germination" is the emergence of the radicle or root from the embryo.

"Field planting" is the establishment of laboratory, greenhouse, nursery, or similar grown planting stock under field conditions.

"Initiation" is the initial cellular proliferation or morphogenic development that eventually results in the establishment of a culture from an explant.

A "(Liquid) Suspension Culture" is a culture composed of cells and embryos suspended in a liquid medium, usually agitated on a gyrotory shaker. An embryogenic suspension culture in conifers is usually composed of both cells and early stage somatic embryos with well-formed suspensor cells and dense cytoplasmic head cells that float freely in the liquid medium.

"Maintenance" is the step in which cultures are grown and maintained in a proliferative phase by sequential subculture to fresh medium at regular intervals after the initiation step. Cultures are grown and maintained as embryogenic tissue on a gelled medium or in a liquid medium as a suspension culture.

"Pre-stage 3 embryos" are differentiated pre-cotyledonary embryos (i.e., Stage 1 or Stage 2 embryos).

"Selected (embryogenic) tissue" is tissue which has been cultured on selection medium so as to select for transgenic tissue (i.e., tissue which has been genetically transformed).

A "selection gene" is a gene whose activity allows cells to grow well in a selection culture medium only if the cells have incorporated the gene, while cells which have not incorporated the gene grow more slowly, do not grow, or are killed.

A "selection medium" is a tissue culture medium which: 1) incorporates a toxin to which a selection gene confers resistance to transformed cells, 2) is composed such that a component necessary for growth of cells is absent and must be provided by transformed cells that have incorporated a selection gene, 3) is composed such that a component necessary for growth is present in a form which can only be taken up or metabolized by transformed cells which have incorporated a selection gene, and/or 4) is composed such to allow preferential growth of transformed cells that have incorporated the selection gene.

"Stage 1 embryos" are small differentiated embryos consisting of an embryonic region of small, densely cytoplasmic region subtended by a suspensor comprised of long, highly vacuolated cells.

"Stage 2 embryos" are further differentiated embryos with a prominent embryonic region that becomes more opaque and assumes a smooth and glossy surface.

"Stage 3 embryos" are further differentiated embryos which show visible cotyledonary primordia.

"Target tissue" is tissue to be subjected to bombardment by carrier particles carrying copies of a genetic construction.

The following examples are provided to further illustrate the present invention and are not to be construed as limiting the invention in any manner.

EXAMPLE 1

This example teaches a method for genetically engineering conifers. In particular, this example teaches a method which includes the steps of pretreatment of embryogenic cultures with preparation medium, gene transfer via particle bombardment, recovery, and selection of transgenic embryogenic tissues on selection agent to produce stably transformed embryos and, subsequently, genetically engineered hybrid pine (*Pinus rigida×P. taeda*) trees. The use of preparation medium in this example was demonstrated to greatly increase the frequency of recovery of transformed material.

Immature seed cones were collected from several different hybrid (*Pinus rigida×P. taeda*) pine sources located in Westvaco's S.C. coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. Where the cones were stored for more than two weeks at 4° C., they were aired and dried out weekly (placed at 23° C., ambient laboratory conditions for two to three hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium.

The present method is not limited to any single basal culture nutrient medium formulation. For example, three common basal culture media formulations which are suitable for use in the present method are listed in Table I below. However, it should be understood that any nutrient media commonly used in Pinus somatic embryogenesis will be suitable for use with this method.

TABLE I

Basal Culture Media Formulations

| COMPONENT | DCR | WV5 | MSG |
|---|---|---|---|
| | CONCENTRATION, mg/l | | |
| INORGANIC SALTS | | | |
| $NH_4NO_3$ | 400.00 | 700.00 | 0 |
| $KNO_3$ | 340.00 | 259.00 | 100.00 |
| $Ca(NO_3)_2 4H_2O$ | 556.00 | 963.00 | 0 |
| $MgSO_4 7H_2O$ | 370.00 | 1850.00 | 370.00 |
| $KH_2PO_4$ | 170.00 | 270.00 | 170.00 |
| $NH_4H_2PO_4$ | 0 | 0 | 0 |
| $CaCl_2 2H_2O$ | 85.00 | 0 | 440.00 |
| KCl | 0 | 1327.00 | 745.00 |
| KI | 0.83 | 0.83 | 0.83 |
| $H_3BO_3$ | 6.20 | 31.00 | 6.20 |
| $MnSO_4 H_2O$ | 22.30 | 15.16 | 16.90 |
| $ZnSO_4 7H_2O$ | 8.60 | 8.60 | 8.60 |
| $Na_2MoO_4 2H_2O$ | 0.25 | 0.25 | 0.25 |
| $CuSO_4 5H_2O$ | 0.25 | 0.25 | 0.03 |
| $CoCl_2 6H_2O$ | 0.03 | 0.03 | 0.03 |
| $NiCl_2 6H_2O$ | 0.03 | 0 | 0 |
| $FeSO_4 7H_2O$ | 27.80 | 27.80 | 27.80 |
| $Na_2EDTA$ | 37.30 | 37.30 | 37.30 |
| VITAMINS, AMINO ACIDS | | | |
| Nicotinic acid | 0.50 | 0.50 | 0.50 |
| Pyridoxine HCl | 0.50 | 0.50 | 0.10 |
| Thiamine HCl | 1.00 | 1.00 | 0.10 |
| Glycine | 2.00 | 2.00 | 0 |

The complete formulations of the media employed in the Examples are listed in Table II below.

TABLE II

Initiation, Maintenance, and Preparation Media Formulations

| COMPONENT | Semi-Solid Initiation Medium $DCR_1$ | Semi-Solid Initiation Medium $WV5_1$ | Semi-Solid Maintenance Medium $DCR_1$ | Liquid Maintenance Medium $DCR_2$ | Semi-Solid Preparation Medium $DCR_3$ |
|---|---|---|---|---|---|
| Basal medium[a] | DCR | WV5 | DCR | DCR | DCR |
| CONCENTRATION (g/l) | | | | | |
| Inositol | 0.50 | 0.50 | 0.50 | 0.50 | 0.50 |
| Casein hydrolysate | 0.50 | 0.50 | 0.50 | 0.50 | 0.50 |
| L-glutamine | 0.25 | 0 | 0.25 | 0.25 | 0.25 |
| Sucrose | 30.00 | 0 | 30.00 | 30.00 | 0 |
| Maltose | 0 | 30.00 | 0 | 0 | 30.00 |
| Polyethylene glycol | 0 | 0 | 0 | 0 | 70.00 |
| GELRITE[b] | 1.5 | 1.5–2.0 | 2.00 | 0 | 2.00 |
| Activated Carbon | 0 | 0 | 0 | 0.5 | 0 |
| CONCENTRATION (mg/l) | | | | | |
| Auxin[c] | 3.00 | 1.0–3.0 | 3.00 | 3.00 | 3.00 |
| Cytokinin[d] | 0.50 | 0.50 | 0.50 | 0.50 | 0.50 |
| Abscisic Acid | 0 | 10.00 | 0 | 0 | 0 |

[a]Refer to Table I for composition of basal medium.
[b]GELRITE (gellan gum manufactured by Merck, Inc.)
[c]2,4-dichlorophenoxyacetic acid (2,4-D) or naphthalene acetic acid (NAA).
[d]$N^6$-benzylaminopurine (BAP) or $N^6$-benzyladenine (BA).

The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into each 100×15 mm sterile plastic petri dish.

Embryogenic tissue cultures from the hybrid pine sources were initiated on semi-solid $DCR_1$ initiation medium (Table II). The dishes were incubated in the dark at a constant temperature of 23° C. After about seven to 21 days, embryogenic tissue extruded from the micropyle of the megagametophyte explants. After about 28 days in culture embryogenic tissue was removed from responsive megagametophyte explants and moved to a new position on the same culture dish, or the embryogenic tissue was transferred to a new culture dish containing the same culture medium as used for initiation. Each individual culture derived from an individual megagametophyte explant was kept separate and assigned a cell line identification code.

Once cultures were extruded and subcultured, they were maintained on $DCR_1$. After 10–22 months on this semi-solid maintenance medium, the tissue cultures were placed in $DCR_2$ liquid maintenance medium containing activated carbon (Table II). These were maintained by subculturing to fresh $DCR_2$ liquid medium every one to two weeks.

To prepare for gene transfer, a sterile fabric support (here NITEX, commercially available from Sefar Inc.) was placed in a sterile Buchner funnel and one to five milliliters of embryogenic suspension was pipetted onto the fabric support such that the embryogenic tissue was evenly distributed over the surface. The liquid medium was suctioned from the tissues using a mild vacuum. The fabric support with embryogenic tissue was removed from the Buchner funnel and placed on a GELRITE solidified $DCR_3$ preparation medium (Table II) in 100×25 mm plastic petri dishes. Dishes were incubated in a dark growth chamber at 23° C. for about 24 hours.

Figure 1B:
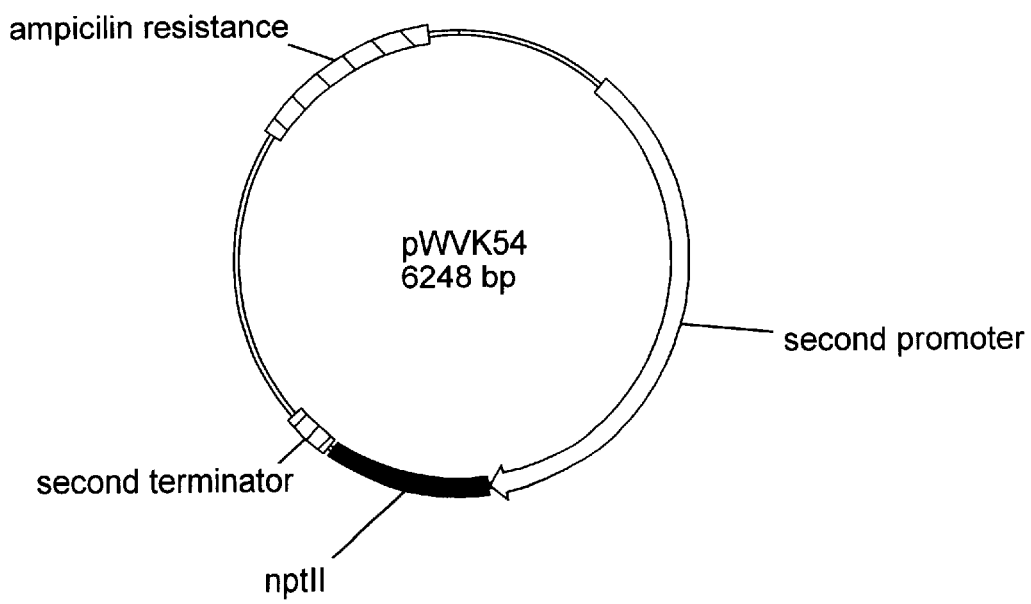
FIG. 1B represents the plasmid pWVK54 which contains a synthetic gene consisting of a second plant promoter sequence, a coding sequence for the selection gene nptII from transposon Tn5, and a second gene terminator sequence.

DNA (genetic construction) was transferred into the tissues and/or embryos via carrier particle (microprojectile) bombardment technology (also known in the industry as Biolistics) using the PDS-1000/He BIOLISTIC Particle Delivery System (available from Bio-Rad Laboratories), which is a preferred method for delivery. The DNAs of interest, here plasmids pWVK49 (FIG. 1A below) containing the visual marker gene uidA and pWVK54 (FIG. 1B below) containing the selection gene nptII, were simultaneously precipitated onto the surface of gold microparticles, which were subsequently accelerated toward the pre-stage 3 embryogenic tissue described above, to penetrate the cell walls. Once inside the cells, DNA is released from the carrier particles and integrated randomly into the chromosomes. The DNA used in this and subsequent examples can be substituted with any suitable DNA sequence.

The gold microcarriers used were 0.6 to 1.6 μm in diameter and were prepared in 50 μl aliquots of 60 mg/ml gold suspended in sterile water, five μl of each plasmid, pWVK49 (1 μg/μl) and pWVK54 (1 μg/μl), 50 μl 2.5 M $CaCl_2$, and 20 μl 0.1M spermidine (free base) The mixture was vortexed for three minutes, centrifuged at 10,000 rpm for 10 seconds and the supernatant was removed. The microcarriers were washed with 250 μl of 70% ethanol, briefly vortexed and centrifuged. After removal of the supernatant the microcarriers were resuspended in 65 μl 100% ethanol. Aliquots of five μl were dispensed onto the center of the macrocarriers and air dried.

In the PDS-1000/He Biolistic device the gap between the rupture disk and the macrocarrier (gap distance) was five mm and the macrocarrier travel distance was 13 mm.

The petri dishes with the fabric support and embryonic tissues were then placed into the interior of the PDS 1000/He Biolistic device and vacuum applied to a level of 28 inches Hg. The gold particles carrying the DNA were accelerated toward the embryogenic tissue following a helium build-up and bursting regulated by a 1550 psi rupture disk. Following DNA transfer the petri dishes containing the fabric support and tissues were incubated in a dark growth chamber at 23° C. for about 24 hours.

The tissues and fabric support were transferred to semi-solid maintenance medium, $DCR_1$ (Table II) to recover from carrier particle bombardment and incubated in a dark growth chamber at 23° C. for a period of about seven days. The tissues and fabric support were transferred to a selection medium, semi-solid maintenance medium $DCR_1$ containing a level of selection agent inhibitory to the growth of non-transformed cells. In this and subsequent examples the selection agent used was GENETICIN at 15 mg/l. The plates were incubated in a dark growth chamber at 23° C. for about six to twelve weeks with the fabric supports containing the tissues being transferred to the same fresh culture medium every three weeks.

Active growth on the selection medium occurred in a number of isolated sectors on some of the petri dishes. Such active growth in the presence of selection agent is an indication that the growing tissues have integrated the selection gene into their chromosomes and are stably transformed. These areas of active growth were treated as independent transformation events and are henceforth referred to as sublines. The transgenic embryogenic tissue was multiplied by transferring growing transgenic sectors to fresh semi-solid maintenance $DCR_1$ medium supplemented with selection agent. Dishes were incubated in a dark growth chamber at 23° C. The actively growing transgenic embryogenic tissue was transferred to fresh semi-solid maintenance $DCR_1$ medium supplemented with selection agent at three week intervals for a period of about six to twelve weeks depending on the rate of growth of the individual sublines of the transgenic embryogenic tissue.

Individual sublines of the transgenic embryogenic tissue were transferred to $DCR_2$ liquid culture medium (Table II) for further multiplication. The cultures were incubated in a dark growth chamber at 23° C. and maintained by subculturing to fresh $DCR_2$ liquid medium every one to two weeks until sufficient multiplication of the tissue had occurred to allow for the subsequent development step.

Using the methods described above, tissues were transferred to a sterile fabric support and subsequently the fabric and tissues were transferred to a $MSG_2$ development medium (see Table III below) containing about 125 mg/l of ABA and no activated carbon and no polyethylene glycol. All cultures were incubated at 23° C. in the dark. It is preferred that the cultures be incubated in the dark rather than light condition. After three passages of about three weeks on the $MSG_2$ medium, cotyledonary somatic embryos (stage 3) were visible. Typically, multiple harvests of cotyledonary somatic embryos were made at the end of the second and third transfers onto $MSG_2$ medium.

TABLE III

Development and Germination Media Formulations

| COMPONENT | Development Medium 1 $MSG_2$ | Development Medium 2 $MSG_3$ | Germination Medium $MSG_4$ |
|---|---|---|---|
| Basal medium[a] | MSG | MSG | MSG |
| CONCENTRATION (g/l) | | | |
| Ammonium nitrate | 0 | 0 | 0.80 |
| Inositol | 0.10 | 0.10 | 0.10 |
| L-glutamine | 1.45 | 1.45 | 0 |
| Sucrose | 0 | 0 | 30.00 |
| Maltose | 60.00 | 60.00 | 0 |
| GELRITE[b] | 2.00 | 2.00 | 2.00 |
| Activated carbon | 0–1.25 | 0 | 5.00 |
| Polyethylene glycol[c] | 0–100.00 | 0 | 0 |
| CONCENTRATION (mg/l) | | | |
| ABA[d] | 11–150 | 21 | 0 |

[a]Refer to Table I for composition of basal medium.
[b]GELRITE (gellan gum manufactured by Merck, Inc.).
[c]Polyethylene glycol (molecular weight of 4000).
[d]Abscisic acid.

Harvested stage 3 embryos were converted into acclimatized plants and field planted. Harvested stage 3 embryos on fabric supports were transferred to medium $MSG_3$ (Table III), in petri plates and incubated for about four weeks in the dark at a temperature of 4° C. Next, embryos on their fabric supports were incubated above water in sealed containers for about three weeks in the dark at a temperature of 25° C. Following the above two treatments, embryos on their fabric supports were transferred to medium $MSG_4$ (Table III) and incubated for about three days in the dark at a temperature of 25° C. Embryos were then removed from their fabric supports and placed individually onto the surface of fresh $MSG_4$ medium in petri plates for germination. Germination was conducted in the light at a temperature of 28° C. Germination plates were examined weekly, over a period of about four weeks, and germinating embryos transferred to MAGENTA boxes containing 100 ml of $MSG_4$ medium for conversion to plantlets. MAGENTA boxes containing developing plantlets were incubated in the light at 28° C. for about eight to twelve weeks.

When the plantlets formed epicotyls (newly formed shoots of approximately two to four cm), they were transferred to containers filled with a potting mix [2:1:2 peat:perlite:vermiculite, containing 602 g/m³ OSMOCOTE fertilizer (18-6-12), 340 g/m³ dolomitic lime and 78 g/m³ MICRO-MAX micronutrient mixture (manufactured by Sierra Chemical Co.)]. The plantlets were placed in a shaded greenhouse and misted infrequently for a period of about two weeks. Plantlets were then transferred to outdoor conditions under shade for about four weeks for final acclimatization prior to being moved to full-sun conditions.

Stable transformation was verified through a combination of growth on selection medium, assay for expression of the visual marker gene at several developmental stages including field-grown plants, polymerase chain reaction amplification of specific segments of the transgene DNA sequence at several developmental stages including field-grown plants, and DNA blot hybridization to detect the integration of the transgenes into the genomic DNA. These techniques were carried out using techniques well known to those skilled in the art of molecular biology.

This method has been employed to generate over 1000 transgenic hybrid pine (*Pinus rigida*×*P. taeda*) embryos from which more than 270 plants have been produced and field planted.

EXAMPLE 2

This example teaches a method for genetically engineering conifers. In particular, this example teaches a method which includes the steps of pretreatment of embryogenic cultures with preparation medium, gene transfer via particle bombardment, recovery, and selection of transgenic embryogenic tissues on selection agent to produce stably transformed embryos and, subsequently, genetically engineered loblolly pine (*P. taeda*) trees. The use of preparation medium in this example was demonstrated to greatly increase the frequency of recovery of transformed material.

Immature seed cones were collected from several different loblolly pine sources located in Westvaco's S.C. coastal breeding orchards near Charleston, S.C. The seed cones were collected when the dominant zygotic embryo was at the precotyledonary stage of development.

Using the methods of Example 1, cell cultures containing pre-stage 3 embryogenic tissue were obtained. After one to three months of culture on $DCR_1$ semi-solid maintenance medium, the tissue cultures were cryopreserved. Pieces of the somatic embryogenic tissue and/or pre-stage 3 somatic embryos (about seven to 14 days since their last subculture on culture maintenance medium) were dispersed in liquid $DCR_1$ medium which contained 0.4 molar sorbitol. The amount of embryogenic tissue used was sufficient to result in a 30% suspension. Erlenmeyer flasks containing the suspension were incubated for 24 hours in the dark on a gyrotory shaker (commonly at 100 rpm), and then placed on ice. Five one milliliter aliquots of the cryoprotectant dimethyl sulfoxide (DMSO) were added to the suspension to bring final concentration of DMSO to 10%. One milliliter aliquots of the cell suspension containing DMSO were then transferred to freezing vials, placed in a programmable freezer, and cooled to −35° C. at 0.33° C. per minute. The freezing vials were subsequently immersed in liquid nitrogen inside a cryobiological storage vessel for long-term storage.

Frozen cultures were retrieved by removing individual vials from the cryobiological storage vessel and placed in 38° C. water to rapidly thaw the frozen cell suspension. The thawed cell suspension were aseptically poured from the cryovial onto a sterile fabric support, which was then transferred to $DCR_1$ maintenance medium and incubated at 23° C. for 24 hours to allow the DMSO to diffuse into the medium. The fabric support containing embryogenic tissue was removed from the medium and transferred to new maintenance medium. After growth on this medium for six to 20 weeks, the tissue cultures were placed in $DCR_2$ liquid maintenance medium (Table II) containing activated carbon, and maintained by subculturing to fresh liquid medium every one to two weeks.

To prepare for gene transfer, a sterile fabric support was placed in a sterile Buchner funnel and one to five milliliters of embryogenic suspension was pipetted onto the fabric support such that the embryogenic tissue was evenly distributed over the surface. The liquid medium was suctioned from the tissues using a mild vacuum. The fabric support with embryogenic tissue was removed from the Buchner funnel and placed on a GELRITE solidified $DCR_3$ preparation medium (Table II) in 100×25 mm plastic petri dishes. Dishes were incubated in a dark growth chamber at 23° C. for about 24 hours.

DNA was transferred into the tissues and/or embryos via carrier particle (microprojectile) bombardment technology (also known in the industry as Biolistics) using the PDS-1000/He BIOLISTIC Particle Delivery System (available from Bio-Rad Laboratories), which is a preferred method for delivery. The DNAs of interest, here plasmids pWVK49 (FIG. 1A above) containing the visual marker gene uidA and pWVK54 (FIG. 1B above) containing the selection gene nptII, were simultaneously precipitated onto the surface of gold microparticles, which were subsequently accelerated toward the pre-stage 3 embryogenic tissue described above, to penetrate the cell walls. Once inside the cells, DNA is released from the carrier particles and integrated randomly into the chromosomes.

The gold microcarriers used were 0.6 to 1.6 $\mu$m in diameter and were prepared in 50 $\mu$l aliquots of 60 mg/ml gold suspended in sterile water, five $\mu$l of each plasmid, pWVK49 (1 $\mu g/\mu l$) and pWVK54 (1 $\mu g/\mu l$), 50 $\mu$l 2.5 M $CaCl_2$, and 20 $\mu$l 0.1M spermidine (free base). The mixture was vortexed for three minutes, centrifuged at 10,000 rpm for 10 seconds and the supernatant was removed. The microcarriers were washed with 250 $\mu$l of 70% ethanol, briefly vortexed and centrifuged. After removal of the supernatant the microcarriers were resuspended in 65 $\mu$l 100% ethanol. Aliquots of five $\mu$l were dispensed onto the center of the macrocarriers and air dried.

In the PDS-1000/He Biolistic device the gap between the rupture disk and the macrocarrier (gap distance) was five mm and the macrocarrier travel distance was 13 mm.

The petri dishes with the fabric support and embryonic tissues were then placed into the interior of the PDS 1000/He Biolistic device and vacuum applied to a level of 28 inches Hg. The gold particles carrying the DNA were accelerated toward the embryogenic tissue following a helium build-up and bursting regulated by a 1550 psi rupture disk. Following DNA, transfer the petri dishes containing the fabric support and tissues were incubated in a dark growth chamber at 23° C. for about 24 hours.

The tissues and fabric support were transferred to semi-solid maintenance medium $DCR_1$ (Table II) to recover from Biolistics and incubated in a dark growth chamber at 23° C. for a period of about seven days. The tissues and fabric support were transferred to a DCRI selection medium. The plates were incubated in a dark growth chamber at 23° C. for about six to twelve weeks with the fabric supports containing the tissues being transferred to the same fresh culture medium every three weeks.

Active growth on the selection medium occurred in a number of isolated sectors on some of the petri dishes. Such active growth in the presence of selection agent is an indication that the growing tissues have integrated the selection gene into their chromosomes and are stably transformed. These areas of active growth were treated as independent transformation events and are henceforth referred to as sublines. The transgenic embryogenic tissue was multiplied by transferring growing transgenic sectors to fresh $DCR_1$ selection medium. Dishes were incubated in a dark growth chamber at 23° C. The actively growing transgenic embryogenic tissue was transferred to fresh semi-solid maintenance $DCR_1$ medium supplemented with selection agent at three week intervals for a period of about six to twelve weeks depending on the rate of growth of the individual sublines of the transgenic embryogenic tissue.

Individual sublines of the transgenic embryogenic tissue were transferred to $DCR_2$ liquid culture medium (Table II) for further multiplication. The cultures were incubated in a dark growth chamber at 23° C. and maintained by subculturing to fresh $DCR_2$ liquid medium every one to two weeks until sufficient multiplication of the tissue had occurred to allow for the subsequent development step.

Using the methods described above, tissues were transferred to a sterile fabric support and subsequently the fabric and tissues were transferred to a $MSG_2$ development medium (Table III) containing about 125 mg/l of abscisic acid (ABA), 1.25 gm/l activated carbon, 70 gm/l polyethylene glycol (PEG), or to a $MSG_3$ development medium with no activated carbon. All cultures were incubated at 23° C. in the dark. It is preferred that the cultures be incubated in the dark rather than light condition. After three passages of about three weeks on the development media, cotyledonary somatic embryos (stage 3) were visible. Typically, multiple harvests of cotyledonary somatic embryos were made at the end of the second and third transfers onto development media.

Harvested stage 3 embryos were converted into acclimatized plants and field planted. Harvested stage 3 embryos on fabric supports were transferred to medium $MSG_3$ (Table III), in petri plates and incubated for about four weeks in the dark at a temperature of 4° C. Next, embryos on their fabric supports were incubated above water in sealed containers for about three weeks in the dark at a temperature of 25° C. Following the above two treatments, embryos on their fabric supports were transferred to medium $MSG_4$ (Table III) and incubated for about three days in the dark at a temperature of 25° C. Embryos were then removed from their fabric supports and placed individually onto the surface of fresh $MSG_4$ medium in petri plates for germination. Germination was conducted in the light at a temperature of 28° C. Germination plates were examined weekly, over a period of about four weeks, and germinating embryos transferred to MAGENTA boxes containing 100 ml of $MSG_4$ medium for conversion to plantlets. MAGENTA boxes containing developing plantlets were incubated in the light at 28° C. for about eight to twelve weeks.

When the plantlets formed epicotyls (newly formed shoots of approximately two to four cm), they were transferred to containers filled with a potting mix [2:1:2 peat:perlite:vermiculite, containing 602 g/m$^3$ OSMOCOTE fertilizer (18-6-12), 340 g/m$^3$ dolomitic lime and 78 g/m$^3$ MICRO-MAX micronutrient mixture (manufactured by Sierra Chemical Co.)]. A number of plantlets were placed in a shaded greenhouse and misted infrequently for a period of about two weeks. Plantlets were then transferred to outdoor conditions under shade for about four weeks for final acclimatization prior to being moved to full-sun conditions.

Stable transformation was verified through a combination of growth on selection medium, assay for expression of the visual marker gene at several developmental stages including plants prepared for field testing, and polymerase chain reaction amplification of specific segments of the transgene DNA sequence at several developmental stages including plants prepared for field testing. These techniques were carried out using techniques well known to those skilled in the art.

These methods have been used to produce thousands of transgenic embryos of loblolly pine (*Pinus taeda*). A subset of these transgenic embryos have been made into plants and prepared for field planting.

EXAMPLE 3

This example illustrates the general applicability of the invention across a broad range of cell lines of both loblolly pine (*Pinus taeda*) and hybrid pine (*Pinus rigida*×*P. taeda*).

To determine the applicability of the current invention over a diverse range of genetic materials, a total of 73 cell lines of loblolly pine and five cell lines of hybrid pine somatic embryogenic cultures containing pre-stage 3 embryos were produced and transformed using the methods described in Examples 1 and 2 above. These included one cell line each of loblolly pine and hybrid pine in the procedures as control (i.e., reference) material. These control cell lines were known to be responsive to the genetic transformation procedures as they were found to be transformable using the methods of the previous examples. The remaining 72 loblolly and four hybrid pine cell lines had not been previously tested. The cell lines subjected to the above procedure were microscopically examined and found to contain pre-stage 3 embryos prior to gene transfer.

The ability to transform cell lines was assessed by a variety of methods. The ability to grow on selection medium in which the concentration of selection agent inhibits the growth of non-transformed cell lines was one criterion for transformation. Another criterion for transformation was detection of the visual marker gene supplied by the plasmid pWVK49. Another criterion for transformation was the detection of either transgene as determined by polymerase chain reaction. These methods are well known to those skilled in the art of molecular biology.

As shown in Table IV below, of the 72 loblolly pine and four hybrid pine test lines subjected to the procedure, 19 loblolly pine and two hybrid pine cell lines produced sublines capable of growth on selection medium. These comprise at least 26% of loblolly pine cell lines and 50% of hybrid pine cell lines tested. Eighty-seven sublines of embryogenic tissue were recovered from the 19 loblolly pine cell lines and three sublines were recovered from the two hybrid pine cell lines.

TABLE IV

Frequency of Stable Transformations for Loblolly Pine and Hybrid Pine Cell Lines.

|  | Loblolly pine | Hybrid pine |
| --- | --- | --- |
| Number of lines tested | 72 | 4 |
| Number of lines giving rise to at least one transformed subline | 19 | 2 |
| Total number of transformed sublines recovered | 87 | 3 |

To determine the frequency that transformed sublines of pine tissue stably integrated DNA sequences from either or both plasmids used (pWVK49 and pWVK54) during gene transfer, DNA was isolated from a portion of the transformed sublines prior to their transfer to $MSG_2$ development medium and subjected to polymerase chain reaction analysis. The sublines subjected to analysis included the 87 loblolly pine sublines described above in Table IV as well as sublines obtained from the loblolly pine and hybrid pine control cell lines described above for a total of 173 sublines. These results are shown in Table V below.

TABLE V

Frequency of Stable Transformation and Co-Transformation for Loblolly Pine and Hybrid Pine Sublines

| Sequences detected | Number positive/ number tested | Percentage |
| --- | --- | --- |
| uidA and nptII | 136/173 | 79% |
| uidA only | 1/173 | <1% |
| nptII only | 18/173 | 10% |

These data show a high frequency of co-transformation. Sequences for both transgenes, uidA and nptII, were detected in 79 percent of the sublines tested. Only one subline (less than one percent) contained only the uidA visual marker gene. Ten percent of the tested sublines contained only the nptII selection gene. In the remaining 19 sublines, no transgenes were detected by polymerase chain reaction.

A subset of the loblolly pine sublines obtained above were further developed and germinated according to the methods of examples 1 and 2. Samples of developing embryos at various stages of development as well as plants prepared for field planting were tested for expression of the visual marker gene and/or the selection gene. Samples were also tested for the presence of the transgenes using polymerase chain reaction analysis. For each of the above tests, positive results indicative of stable transformation were obtained. The test methods used above are well known to those skilled in the art of molecular biology.

EXAMPLE 4

In this example, additional preparation media formulations and alternative selection steps were employed to recover stably transformed embryogenic tissue of loblolly pine (*Pinus taeda L.*) and hybrid pine (*Pinus rigida*×*P. taeda*).

Embryogenic cultures initiated as described in previous examples from three different families of loblolly pine (including one that has been recalcitrant to transformation using the methods of the previous examples) and three lines of hybrid pine were prepared for bombardment by plating on $DCR_3$ as described in previous examples, or subjected to the same manipulations using alternative preparation media as described in Table VI below. Preparation media were developed using DCR or MSG basal media as described in Tables I, II and III above. This example demonstrates that the present invention is not restricted to any particular basal medium formulation, but may be based on any medium suitable for pine embryogenic culture. Liquid preparation media were also employed. For cultures prepared in liquid preparation media, the liquid maintenance medium $DCR_2$ was pipetted off the settled cells and replaced with an equal volume of liquid preparation medium, in which the cultures were allowed to grow until they were plated onto the same medium to which GELRITE had been added in order to facilitate bombardment.

TABLE VI

Examples of Preparation Media Formulations

Preparation Medium Formulation

| Concentration in g/l: | A | B | C | D | E | F | G | H | I | J |
|---|---|---|---|---|---|---|---|---|---|---|
| Sucrose | 0 | 60 | 30 | 30 | 30 | 30 | 30 | 0 | 30 | 30 |
| Maltose | 60 | 0 | 0 | 0 | 0 | 0 | 0 | 30 | 0 | 0 |
| Inositol | 0.5 | 0.5 | 0.5 | 0.5 | 0.5 | 0.5 | 0.5 | 0.5 | 0.5 | 45 |
| Polyethylene glycol | 70 | 0 | 0 | 0 | 0 | 0 | 0 | 0 | 0 | 0 |
| Glycerol | 0 | 0 | 0 | 0 | 0 | 46 | 46 | 46 | 0 | 0 |
| Sorbitol | 0 | 0 | 46 | 91 | 182 | 0 | 0 | 0 | 0 | 0 |
| GELRITE | 2 | 2 | 2 | 0 | 2 | 2 | 0 | 2 | 5 | 2 |

On the day following bombardment, cultures were transferred to $DCR_1$ for one week, and then onto selection medium as described in the previous examples for selection of stable transformants. However, the bombarded target tissue was transferred onto fresh selection medium at intervals of two weeks rather than the three week subculture interval used in previous examples. This example serves to show that any suitable subculture interval may be used.

Tissues were examined for actively growing sectors at six and twelve weeks after bombardment. Actively growing stable sublines were observed in tissue that had been prepared on each of these media. A subset of these lines, including both *P. taeda* and hybrid pine cultures, were confirmed as transformed using assay of a visual marker and polymerase chain reaction analysis for sequences from the transforming DNA.

This example shows that a variety of preparation media are effective in allowing detectable frequencies of stable transformation. Both stable transformation and embryo development are necessary for the production of stably transformed pine plants, an object of this invention. Therefore, in order to determine the effects of the addition of organic alcohols and higher sugar concentrations in the preparation media on subsequent regeneration of plants, control tissue (not subsequently bombarded or cultured on selection media) was cultured in liquid or solid preparation media containing added organic alcohols or higher sugar or gelling agent concentrations (as described in Table VI above). After 9 weeks of culture on $MSG_2$ development medium, during which the tissues were transferred to fresh media every three weeks as described in the previous examples, stage 3 embryos deemed suitable for germination were counted and harvested. The results are listed in Table VII below.

TABLE VII

Effect of Preparation Media on Stage 3 Embryo Development

| | Formulation No. | | | | | | |
|---|---|---|---|---|---|---|---|
| | A | B | C | D | E | F | J |
| LOB Family E | 14[1] | 28 | 11 | 28 | 0 | 11 | 0 |
| LOB Family K | 31 | 95 | 23 | 1 | 38 | 74 | 1 |
| LOB Family B | 12 | 20 | 35 | 47 | n.d.[2] | n.d. | 0 |
| P × L Family A | 39 | 18 | n.d. | n.d. | 9 | 9 | n.d. |

[1]Results shown are the average number of high quality harvestable stage 3 embryos produced per tissue culture plate.
[2]n.d. = not determined.

Table VII demonstrates that an elevated inositol treatment (media formulation J) taught as being useful for the transformation of spruce (Clapham et al. 1995) has been found not to be effective for the preparation of pine (as the elevated inositol disrupted embryo development across all the genetic backgrounds tested). In contrast, the other preparation treatments did not show disruption of embryo development across all tested lines.

EXAMPLE 5

In this example, the method taught by Ellis in U.S. Pat. No. 5,681,730 as being effective for transforming conifers, specifically white spruce, was tested and compared for effectiveness in initiating embryogenic cultures of loblolly pine for use in genetic transformation. It is well known by researchers that there are significant differences between spruce and pine species in the ability to undergo somatic embryogenesis. Protocols that are effective with spruce may not be effective with pine. Furthermore, spruce is considered to be an "easy" system for somatic embryogenesis, whereas pines are generally considered to be much more "recalcitrant."

Immature seeds from two open pollinated families of loblolly pine (Pinus taeda) were used in the experiment. The seed sources were coded "A" and "J." Immature cones containing seeds with the appropriate stage of zygotic embryo development were collected and stored for one to two weeks at 4° C., as described in Example 1 above, until initiation according to the treatments described below.

Method E-1 utilized the method exactly as taught by Ellis in U.S. Pat. No. 5,681,730 as being effective for white spruce, with the only difference being that loblolly pine (Pinus taeda) embryos were used (Table VIII). As taught by Ellis, immature zygotic embryos at just after emergence of the cotyledons (stage 3) were placed longitudinally on the surface of the culture initiation medium as described by Hakman and Fowke (1987) and Webb et al. (1989). The culture initiation medium was that of von Arnold and Eriksson (1981), supplemented with 1% sucrose, solidified with 0.6% Difco-bacto agar, 10 $\mu$M 2,4-dichlorophenoxyacetic acid (2,4-D), and 1 $\mu$M $N^6$-benzyladenine (BA). The explants were cultured for 8 weeks under fluorescent light levels of 25 to 40 $\mu Em^{-2}s^{-1}$, on a 16 hr photoperiod, at 25° C. (Webb et al. 1989). Embryogenic tissues proliferating from these explants were placed in the dark and subcultured on the same medium as noted above every 3 weeks.

Method E-2 used the processes and media taught by Ellis in U.S. Pat. No. 5,681,730 exactly as noted for Method E-1 above with the sole exception that, instead of using zygotic embryos at just after emergence of the cotyledons (as taught by Ellis for spruce), the stage and type of explant known to work optimally for initiation of embryogenic tissue of pines was utilized (Becwar and Pullman 1995)—namely immature megagametophytes containing dominant zygotic embryos at the pre-cotyledonary developmental stage (pre-stage 3).

Method A-3 used the same stage and type of explants employed in Method E-2 (i.e., megagametophyte explants containing pre-stage 3 zygotic embryos), but the methods and media employed with these explants are those taught in the present invention. The pre-stage 3 zygotic embryos were cultured on $WV5_1$ initiation medium containing 3 mg/L 2,4-D and 0.5 mg/L BA, and 1.5 g/L GELRITE (see Table II). Proliferating embryogenic cultures from Method A-3 were maintained on the $WV5_1$ medium as above, except that it contained 30 g/L sucrose and 2.0 g/L GELRITE. They were also subcultured at 3 week intervals. The differing culture initiation methods employed are listed in Table VIII below.

TABLE VIII

Culture Initiation Methods

| Method | Explant (Pinus taeda) | Initiation Medium | Light, photoperiod, etc. |
|---|---|---|---|
| E-1 | Stage 3 ZE[1] with cotyledons | Ellis[3] | Ellis |
| E-2 | MG[2] with pre-stage 3 ZE | Ellis | As in Example 1 |

TABLE VIII-continued

Culture Initiation Methods

| Method | Explant (Pinus taeda) | Initiation Medium | Light, photoperiod, etc. |
|---|---|---|---|
| A-3 | MG with pre-stage 3 ZE | $WV5_1$ (Table II) | As in Example 1 |

[1]ZE = zygotic embryo.
[2]MG = megagametophyte.
[3]Ellis = As taught by Ellis in U.S. Pat. No. 5,681,730.

The number of explants with proliferating embryogenic tissue was determined at 6 to 8 weeks after the start of the experiment. A statistical analysis was used to test for treatment and seed source differences in the frequency of proliferating embryogenic tissue.

There was a significant treatment effect on culture initiation as measured by the number of responsive explants (Table IX). Culture initiation occurred at much higher frequencies in Method A-3 than in either Method E-1 or Method E-2. Both seed families responded similarly, although J was more responsive than A. This was expected, as past experiments have shown it to be somewhat more difficult to induce embryogenic cultures from seed family A than from seed family J.

TABLE IX

Results of Method Comparisons

| Seed Family | Method Utilized | Type of Explant (Pinus taeda) | No. of Explants | No. and (%) of Explants with proliferating $ET^1$ after 6–8 weeks |
|---|---|---|---|---|
| A | E-1 | Stage 3 $ZE^2$ with cotyledons | 128 | 1 (1%) |
| A | E-2 | $MG^3$ with pre-stage 3 ZE | 104 | 0 (0%) |
| A | A-3 | MG with pre-stage 3 ZE | 112 | 32 (29%) |
| J | E-1 | Stage 3 ZE with cotyledons | 120 | 0 (0%) |
| J | E-2 | MG with pre-stage 3 ZE | 120 | 1 (1%) |
| J | A-3 | MG with pre-stage 3 ZE | 120 | 92 (77%) |

[1]ET = embryogenic tissue.
[2]ZE = zygotic embryo.
[3]MG = megagametophyte.

For explants from seed family A, the method taught in Ellis in U.S. Pat. No. 5,681,730 (Method E-1) resulted in the production of one explant which showed proliferation of embryogenic tissue at six weeks. This one culture was transferred to new medium, where it died and did not proliferate further. Likewise, the method taught by Ellis when employed with pre-stage 3 zygotic embryos (Method E-2) resulted in no explants being produced which showed proliferation of embryogenic tissue at six weeks.

As for explants from seed family J, the method taught in Ellis in U.S. Pat. No. 5,681,730 (Method E-1) resulted in no explants being produced which showed proliferation of embryogenic tissue at six weeks. Likewise, the method taught by Ellis when employed with pre-stage 3 zygotic embryos (Method E-2) resulted in the production of one explant which showed proliferation of embryogenic tissue at six weeks. This one culture was transferred to new medium, where it died and did not proliferate further.

Thus, no embryogenic cultures of loblolly pine were established using either Method E-1 or Method E-2. Indeed, our comparison results indicate that one would not obtain embryogenic cultures of pine for genetic transformation using the protocol taught by Ellis in U.S. Pat. No. 5,681,730. It is believed that this lack of effectiveness in pine is probably due both the employment of an inappropriate stage of embryo explant and the use of inappropriate tissue culture media.

In contrast, numerous vigorous embryogenic cultures were established from both a difficult seed family (A) and a more responsive family (J) using the methods taught in the present invention.

EXAMPLE 6

This example describes a method of initiating secondary embryogenic cultures of Southern pines from individual pre-stage 3 embryos, including embryos which have been genetically transformed. In this example, secondary embryogenic cultures are initiated from pre-stage 3 somatic embryos arising from different types of cultures. Furthermore, cultures containing visible pre-stage 3 embryos served as the targeted tissue for genetic transformation, and it was demonstrated that cultures lacking visible pre-stage 3 embryos did not give rise to stable transformants.

The system of targeting individual stage 3 (cotyledonary) embryos for genetic transformation (as taught by Ellis for white spruce in U.S. Pat. No. 5,681,730) has been found not to be effective with pines (Example 5 above) because it has not been possible to efficiently initiate secondary embryogenic cultures from stage 3 embryos (somatic or zygotic) of pine species. However, pine embryogenic cultures can be efficiently initiated from very early stage (pre-stage 3) zygotic embryos (Becwar and Pullman 1995). This example teaches that they can also be initiated from very early stage (pre-stage 3) somatic embryos.

Embryos for use in this method can be derived from several sources, including, but not limited to: embryogenic cultures previously initiated from immature seed explants (megagametophytes containing immature zygotic embryos), embryogenic cultures derived from immature zygotic embryo explants, embryogenic cultures grown on embryo development medium, and liquid embryogenic suspension cultures. For this method to be successful, the explants or cultures must contain embryos that are pre-stage 3 in development, according to the embryo staging system of Hakman and von Arnold (1988).

Newly initiated (7 week old) embryogenic cultures from three genetically different parent trees of loblolly pine (*Pinus taeda*) were used as a source of pre-stage 3 somatic embryos for this experiment. The cultures had been initiated from immature seeds on $WV5_1$ initiation medium as listed in Table II, according to the methods described in previous examples.

To initiate secondary embryogenic cultures from individual pre-stage 3 embryos, the extruded mass of embryogenic tissue, containing pre-stage 3 somatic embryos, was dissected with fine-tipped forceps to remove individual pre-stage 3 somatic embryos with attached suspensor cells. These isolated pre-stage 3 somatic embryos were placed on maintenance medium $DCR_1$, as listed in Table II except that the medium contained 10 mg/l abscisic acid. Sixteen to 40 somatic embryos from the newly extruded embryogenic tissue of each immature seed were cultured (8 per each 100×15 mm plastic petri plate). Every 14 to 21 days, vigorously proliferating secondary embryogenic tissue derived from the isolated pre-stage 3 somatic embryos was transferred to fresh medium of the same type ($DCR_1$). The amount of embryogenic tissue proliferation was quantified by measuring the size of each pre-stage 3 somatic embryo-derived mass of tissue with an image analysis system. Data were recorded at 38 days after beginning the experiment with 16 to 40 somatic embryos per each seed source and $DCR_1$ medium, and the results are listed in Table X below.

TABLE X

Frequency and Mean Size of Secondary Embryogenic Tissue Proliferating from Pre-stage 3 Somatic Embryos.

| Seed source | Percent proliferation | Mean proliferation size (mm²) |
| --- | --- | --- |
| X-1 | 75% | 122 |
| X-2 | 72% | 109 |
| X-3 | 97% | 123 |
| X-4 | 97% | 145 |
| B-1 | 67% | 61 |
| B-2 | 69% | 62 |
| B-3 | 88% | 182 |
| J-1 | 30% | 6 |
| J-2 | 10% | 5 |
| J-3 | 85% | 68 |
| J-4 | 35% | 15 |
| Average: | 66% | 82 |

Several secondary embryogenic cultures (sublines) initiated from the pre-stage 3 somatic embryos were used to regenerate stage 3 somatic embryos, by the methods described in previous examples, and thereby verify that the cultures were indeed embryogenic and therefore could be used to regenerate pine trees. Briefly, secondary cultures derived from individual pre-stage 3 somatic embryos were used to establish liquid suspension cultures as described in previous examples, and aliquots of these suspensions were plated on embryo development medium $MSG_2$ (Table III) as described in previous examples. Stage 3 somatic embryos were harvested from the embryo development medium and three plates per individual pre-stage 3 embryo source were counted. The results are listed in Table XI below.

TABLE XI

Production of Harvestable Stage 3 (Cotyledonary) Somatic Embryos

| Cell line | Total number harvested |
| --- | --- |
| X-1 | 18 |
| X-2 | 288 |
| X-4 | 45 |
| B-3 | 111 |

In another experiment, pre-stage 3 somatic embryos were obtained from embryogenic cultures growing on embryo development medium ($MSG_2$). Aliquots from suspension cultures derived as described in previous examples were pipetted onto a sterile fabric support in a sterile Buchner funnel, such that the embryogenic tissue was distributed over its surface. The liquid medium was suctioned from the tissues using a mild vacuum and the fabric bearing embryogenic tissue was removed from the Buchner funnel and placed on $MSG_2$ development medium (see Table III above) in 100×25 mm plastic petri dishes. Dishes were incubated in a dark growth chamber at 23° C. for about three to six weeks. At this point, pre-stage 3 embryos with attached suspensor cells could be aseptically separated from the subtending tissue using a dissecting microscope and fine-tipped forceps as described above. These were placed on maintenance medium $DCR_1$ as described above. As in the previous experiment, pre-stage 3 somatic embryos initiated embryogenic tissue at a high frequency and produced large masses of embryogenic tissue.

Thus, this method was successful at initiating embryogenic cultures from individual pre-stage 3 somatic embryos of loblolly pine obtained from a variety of sources, and the resulting cultures can produce somatic embryos for use in regenerating pine trees. These results serve as the basis for using pre-stage 3 somatic embryos of pine as target tissue for genetic transformation.

For transformation, embryogenic cultures were initiated from immature seed from several different loblolly pine and hybrid pine sources as described above. In this example, the initiation media contained either 1.0 mg/l naphthalene acetic acid (NAA) or 3.0 mg/l 2,4-dichlorophenoxyacetic acid (2,4-D), and also contained 10 mg/l abscisic acid. This example is intended to show that the present method is not limited to any single basal culture nutrient medium formulation. It should be understood that any nutrient media commonly used in Pinus somatic embryogenesis may be suitable for use with this method. Once cultures were extruded and subcultured as described in previous examples, some of the cultures were cryopreserved as described in previous examples. These tissue cultures were retrieved from cryostorage as described above and recultured on a nutrient medium as above. Other cultures used in this example were not cryopreserved, but were continually grown on $WV5_1$ media. This example is intended to show that any culture containing multicellular pre-stage 3 embryogenic initials, derived in any manner, may be suitable for use with this method.

Tissues to be transformed were cultured in liquid maintenance medium $DCR_2$ as described in previous examples and then cultured on $MSG_2$, used here as a preparation medium, in a dark growth chamber at 23° C. for about 3–8 weeks. The tissue on $MSG_2$ medium was bombarded using conditions described in previous examples. Following DNA transfer, visible pre-stage 3 embryos were dissected from the bombarded target tissues and placed individually onto $DCR_1$ as described above for secondary proliferation.

Following a period of one to 14 days, when a preponderance of pre-stage 3 embryos dissected from the bombarded target tissue could be seen to be beginning to proliferate secondary embryogenic cell masses, samples to be assayed for transformation were transferred to a selection medium similar to that described in the previous examples except that it contained 10 mg/l abscisic acid. This example serves to show that the method is not limited to a particular selection medium. Any selection media suitable for use with pine cultures and selection genes familiar to those skilled in the art is applicable in the present method.

Samples of isolated pre-stage 3 embryos from each line and the secondary tissue proliferating from them were also cultured on $DCR_1$ maintenance media without selection agent to observe any effect of the bombardment treatment on proliferation. These cultures were transferred to fresh maintenance media every three weeks. Proliferation of these non-selected controls at nine weeks after dissection is recorded in Table XII.

The pre-stage 3 embryos which had been subjected to selection, and any secondary embryogenic tissue proliferating on them, were transferred every three weeks to fresh $DCR_1$ selection media. The number of stable sublines found to be actively growing on selection media at the end of the selection period is listed in Table XII. Putative transformant sublines with sufficient cell mass growing on the selective medium were further confirmed as transformed by use of polymerase chain reaction analysis and sequences from the transforming DNA, via procedures well-known to those skilled in the art.

TABLE XII

Proliferation of Secondary Embryogenic Cultures from Dissected Pre-stage 3 Embryos after Bombardment.

|  | % Secondary Proliferation on Maintenance Medium | Sublines Growing on Selection Medium, with Transformation Confirmed by Polymerase Chain Reaction Analysis |
| --- | --- | --- |
| LOB line B1 | 91% | 1 |
| P × L line D1 | 90% | 2 |
| P × L line D2 | 88% | 1 |

This example shows that sufficient preparation for transformation was achieved by growing the cultures on $MSG_2$, used here as a preparation medium, prior to and during bombardment. That is, where the materials to be targeted have been cultured on $MSG_2$ medium prior to and during bombardment, we observed that transformation frequency was great enough to allow detection of stable transformants. It should be noted that Family B is a superior loblolly pine genetic stock which has been recalcitrant to transformation by the methods used in Examples 1–3 above. For this genetic stock, the use of $MSG_2$ as an alternative preparation medium is beneficial.

After removal of all visible pre-stage 3 embryos from the bombarded target tissue, samples of the remaining tissue, lacking any visible pre-stage 3 embryos, were resuspended in a liquid maintenance medium similar to $DCR_2$, except that activated charcoal was omitted. Using the methods described above, these suspension cultures were plated onto maintenance medium, so that it could be ascertained that there was still living tissue capable of sustained growth in the cultures. Such cultures continued to proliferate for some months after the dissection. These results demonstrate that removing the visible pre-stage 3 embryos did not constitute removal of all tissue that was capable of embryogenic growth.

The results demonstrate that in the mixed cultures containing visible pre-stage 3 embryos, stage 3 embryos, and other embryogenic and non-embryogenic tissue, the target for transformation was specifically the visible pre-stage 3 embryos. No tissue capable of growing on selection media was recovered from bombarded target tissues from which all visible pre-stage 3 embryos had been removed (though this tissue was still capable of sustained growth on maintenance media), while sublines growing on selection media, and confirmed as transformants using polymerase chain reaction analysis, were recovered from the pre-stage 3 embryos that had been dissected from these cultures.

EXAMPLE 7

In this example, mixed cultures containing precotyledonary embryos were dissected prior to bombardment in order to allow pre-stage 3 embryos to serve directly as the targeted tissue.

This example used a subset of the same embryogenic lines used in the previous example. Initiation and maintenance of these cultures using gelled and liquid media was described in the previous example. For each culture to be targeted, cultures were placed on $MSG_2$ medium as described in the previous example. Dishes were incubated in a dark growth chamber at 23° C. for about three to six weeks, until many pre-stage 3 embryos were visible and could be aseptically separated from the subtending tissue using a dissecting microscope and fine-tipped forceps as described in the previous example.

In this example, visible pre-stage 3 embryos were dissected from the tissues and placed onto $DCR_3$ preparation medium for a period of two days prior to bombardment. The isolated pre-stage 3 embryos were targeted for DNA transfer by bombardment as described in previous examples, except that acceleration pressures of 900 and 1800 psi of helium were used. This example serves to show that multiple variations of the Biolistic gene transfer protocol are suitable for use within the present method.

After bombardment the pre-stage 3 embryos were transferred to maintenance medium as described in Example 6 to grow until they could be seen to be beginning to proliferate secondary embryogenic masses as described in Example 6 above. A sample of the dissected pre-stage 3 embryos and tissue proliferating on them were then transferred to selection medium as described in Example 6 above. Non-selected control samples from each line consisted of dissected pre-stage 3 embryos placed onto $DCR_3$ preparation medium for the same periods, and bombarded at the same times, but grown further on maintenance medium rather than on selection medium. Additional control samples of the dissected pre-stage 3 embryos from each line had also been placed onto $DCR_3$ preparation medium for the same periods, but were not bombarded. These controls were grown and transferred to fresh maintenance medium every three weeks, and observed for secondary embryogenic proliferation at three and nine weeks. The selected cultures were transferred at three-weekly intervals to fresh selection medium if active growth of secondary embryogenic sublines on the selection medium could be observed.

The results showed that secondary embryogenic cultures could be proliferated on maintenance medium at frequencies of up to 100% from pre-stage 3 embryos that were isolated and cultured on preparation medium, whether these embryos had been bombarded or not. Additionally, transformant sublines were obtained by this method from a superior loblolly pine genetic stock. These were confirmed as transformed by growth on selection media and by polymerase chain reaction analysis as described in the previous examples. These results demonstrate that isolated pre-stage 3 embryos of pine can serve directly as a sufficient target for transformation. Since each subline is derived from an individual embryo, rather than a mass of embryogenic tissue, this method increases the probability of having genetically homogeneous transgenic cell lines.

Many modifications and variations of the present invention will be apparent to one of ordinary skill in the art in light of the above teachings. It is therefore understood that the scope of the invention is not to be limited by the foregoing description, but rather is to be defined by the claims appended hereto.

What is claimed is:

1. A method for genetically engineering conifers selected from the group consisting of the genus Pinus and Pinus interspecies hybrids, which comprises:
   (a) placing conifer target tissue selected from the group consisting of embryogenic tissue containing pre-stage 3 somatic embryos, pre-stage 3 somatic embryos, pre-stage 3 zygotic embryos, and combinations thereof, on a target surface;
   (b) bombarding the target tissue by physically accelerating at the target tissue carrier particles which are much smaller than the cells of the target tissue, the carrier particles carrying copies of a genetic construction including at least one gene of interest;
   (c) inducing the bombarded target tissue to form proliferative tissue which is capable of forming somatic embryos;
   (d) during the step of inducing, culturing the bombarded target tissue on selection medium so as to select for embryogenic tissue which is transformed by the gene of interest;
   (e) inducing transformed somatic embryos to develop from the selected embryogenic tissue; and
   (f) germinating and converting the transformed somatic embryos thus produced into clonal transgenic conifer plants.

2. The method of claim 1 wherein the conifer is selected from the group consisting of *Pinus taeda, Pinus serotina, Pinus palustris, Pinus elliottii, Pinus rigida, Pinus radiata*, and hybrids thereof.

3. The method of claim 1 wherein the carrier particles are microparticles between 0.2 and 2.0 microns in diameter.

4. The method of claim 1 wherein the selection medium contains a sufficient amount of organic and inorganic nutrients, up to about 5.0 mg/l of auxin, up to about 1.0 mg/l of cytokinin, up to about 30.0 mg/l of abscisic acid, up to about 60.0 g/l of sugar, and wherein the selection medium allows preferential growth of transformed cells containing the gene of interest.

5. The method of claim 4 wherein the selection medium contains a sufficient amount of organic and inorganic nutrients, up to about 5.0 mg/l of auxin, up to about 1.0 mg/l of cytokinin, up to about 30.0 mg/l of abscisic acid, up to about 60.0 g/l of sugar, and wherein the selection medium lacks a component necessary for the growth of non-transformed cells but for which the gene of interest confers to transformed cells the ability to produce the lacking component.

6. The method of claim 4 wherein the selection medium contains a sufficient amount of organic and inorganic nutrients, up to about 5.0 mg/l of auxin, up to about 1.0 mg/l of cytokinin, up to about 30.0 mg/l of abscisic acid, up to about 60.0 g/l of sugar, and wherein the selection medium contains a component necessary for the growth of cells in a form which cannot be utilized by non-transformed cells but for which the gene of interest confers to transformed cells the ability to utilize the necessary component.

7. The method of claim 4 wherein the selection medium contains a sufficient amount of organic and inorganic nutrients, a selection agent at a concentration which is toxic to non-transformed cells but for which the gene of interest confers resistance to transformed cells, up to about 5.0 mg/l of auxin, up to about 1.0 mg/l of cytokinin, up to about 30.0 mg/l of abscisic acid, and up to about 60.0 g/l.

8. The method of any one of claims 4, 5, 6, or 7 wherein the sugar is a member selected from the group consisting of glucose, maltose, sucrose, and combinations thereof.

9. The method of any one of claims 4, 5, 6, or 7 wherein the selection medium further contains a gelling agent selected from the group consisting of about 6.0 to about 9.0 g/l of agar, about 1.75 to about 4.0 g/l of gellan gum, about 6.0 to about 8.0 g/l of agarose, about 3.5 to about 5.0 g/l of AGARGEL, and combinations thereof.

10. The method of claim 1 which further comprises:
  (a) culturing conifer target tissue selected from the group consisting of embryogenic tissue containing pre-stage 3 somatic embryos, pre-stage 3 somatic embryos, pre-stage 3 zygotic embryos, and combinations thereof, on preparation media containing a sufficient amount of inorganic and organic nutrients, up to about 5.0 mg/l of auxin, up to about 1.0 mg/l of cytokinin, up to about 150.0 mg/l of abscisic acid, about 10.0 to about 120.0 g/l of sugar, and up to about 0.5M of organic alcohol, for a sufficient period of time to prepare the target tissue for bombardment by carrier particles;
  (b) placing the prepared target tissue on a target surface;
  (c) bombarding the prepared target tissue by physically accelerating at the prepared target tissue carrier particles which are much smaller than the cells of the target tissue, the carrier particles carrying copies of a genetic construction including at least one gene of interest;
  (d) inducing the bombarded target tissue to form proliferative tissue which is capable of forming somatic embryos;
  (e) during the step of inducing, culturing the bombarded target tissue on selection media so as to select for embryogenic tissue which is transformed by the gene of interest;
  (f) inducing transformed somatic embryos to develop from the selected embryogenic tissue; and
  (g) germinating and converting the transformed somatic embryos thus produced into clonal transgenic conifer plants.

11. The method of claim 1 which further comprises
  (a) placing conifer target tissue selected from the group consisting of embryogenic tissue containing pre-stage 3 somatic embryos, pre-stage 3 somatic embryos, pre-stage 3 zygotic embryos, and combinations thereof, on a target surface;
  (b) bombarding the target tissue by physically accelerating at the target tissue carrier particles which are much smaller than the cells of the target tissue, the carrier particles carrying copies of a genetic construction including at least one gene of interest;
  (c) culturing the bombarded target tissue on preparation medium containing a sufficient amount of inorganic and organic nutrients, up to about 5.0 mg/l of auxin, up to about 1.0 mg/l of cytokinin, up to about 150.0 mg/l of abscisic acid, about 10.0 to about 120.0 g/l of sugar, and up to about 0.5M of organic alcohol, for a sufficient period of time to allow the bombarded target tissue to recover from carrier particle insertion;
  (d) inducing the bombarded target tissue to form proliferative tissue which is capable of forming somatic embryos;
  (e) during the step of inducing, culturing the bombarded target tissue on selection media so as to select for embryogenic tissue which is transformed by the gene of interest;
  (f) inducing transformed somatic embryos to develop from the selected embryogenic tissue; and
  (g) germinating and converting the transformed somatic embryos thus produced into clonal transgenic conifer plants.

12. The method of claim 1 which further comprises:
  (a) culturing conifer target tissue selected from the group consisting of embryogenic tissue containing pre-stage 3 somatic embryos, pre-stage 3 somatic embryos, pre-stage 3 zygotic embryos, and combinations thereof, on preparation media containing a sufficient amount of inorganic and organic nutrients, up to about 5.0 mg/l of auxin, up to about 1.0 mg/l of cytokinin, up to about 150.0 mg/l of abscisic acid, about 10.0 to about 120.0 g/l of sugar, and up to about 0.5M of organic alcohol, for a sufficient period of time to prepare the target tissue for bombardment by carrier particles;
  (b) placing the prepared target tissue on a target surface;
  (c) bombarding the prepared target tissue by physically accelerating at the prepared target tissue carrier particles which are much smaller than the cells of the target tissue, the carrier particles carrying copies of a genetic construction including at least one gene of interest;
  (d) culturing the bombarded target tissue on preparation medium containing a sufficient amount of inorganic and organic nutrients, up to about 5.0 mg/l of auxin, up to about 1.0 mg/l of cytokinin, up to about 150.0 mg/l of abscisic acid, about 10.0 to about 120.0 g/l of sugar, and up to about 0.5M of organic alcohol, for a sufficient period of time to allow the bombarded target tissue to recover from carrier particle insertion;
  (e) inducing the bombarded target tissue to form proliferative tissue which is capable of forming somatic embryos;
  (f) during the step of inducing, culturing the bombarded target tissue on selection media so as to select for embryogenic tissue which is transformed by the gene of interest;
  (g) inducing transformed somatic embryos to develop from the selected embryogenic tissue; and
  (h) germinating and converting the transformed somatic embryos thus produced into clonal transgenic conifer plants.

13. The method of any one of claims 10, 11 or 12 wherein the sugar is a member selected from the group consisting of glucose, maltose, sucrose, and combinations thereof.

14. The method of any one of claims 10, 11 or 12 wherein the organic alcohol is a member selected from the group consisting of glycerol, mannitol, sorbitol, polyethylene glycol, and combinations thereof.

15. The method of any one of claims 10, 11 or 12 wherein the preparation medium further contains a gelling agent selected from the group consisting of about 6.0 to about 9.0 g/l of agar, about 1.75 to about 5.0 g/l of gellan gum, about 6.0 to about 8.0 g/l of agarose, about 3.5 to about 5.0 g/l of AGARGEL, and combinations thereof.

16. The method of claim 1 wherein the target tissue has been retrieved from cryopreservation.

17. The method of claim 1 wherein the bombarded target tissue is cryopreserved and subsequently retrieved from cryopreservation.

18. The method of claim 1 wherein the selected embryogenic tissue is cryopreserved and subsequently retrieved from cryopreservation.

* * * * *

UNITED STATES PATENT AND TRADEMARK OFFICE
CERTIFICATE OF CORRECTION

PATENT NO.     : 6,518,485 B1
DATED          : February 11, 2003
INVENTOR(S)    : Marie B. Connett-Porceddu et al.

It is certified that error appears in the above-identified patent and that said Letters Patent is hereby corrected as shown below:

<u>Title page,</u>
Item [56], OTHER PUBLICATIONS, delete "22(12)2014-2018" and insert therefor -- 22:2014-2018 --.

<u>Column 20,</u>
Line 34, delete 'DCRI" and insert therefor -- $DCR_1$ --.

<u>Column 32,</u>
Line 57, after "60.0 g/l" insert therefore -- of sugar. --

Signed and Sealed this

Tenth Day of June, 2003

JAMES E. ROGAN
*Director of the United States Patent and Trademark Office*